United States Patent
Savage

(10) Patent No.: US 7,264,965 B2
(45) Date of Patent: *Sep. 4, 2007

(54) METHOD FOR PRODUCING OR ENHANCING A T-CELL RESPONSE AGAINST A TARGET CELL USING A COMPLEX COMPRISING AN HLA CLASS I MOLECULE AND AN ATTACHING MEANS

(75) Inventor: Philip Michael Savage, London (GB)

(73) Assignee: Alexis Biotech Limited, London (GB)

( * ) Notice: Subject to any disclaimer, the term of this patent is extended or adjusted under 35 U.S.C. 154(b) by 471 days.

This patent is subject to a terminal disclaimer.

(21) Appl. No.: 10/116,901

(22) Filed: Apr. 5, 2002

(65) Prior Publication Data
US 2003/0044415 A1 Mar. 6, 2003

Related U.S. Application Data

(63) Continuation-in-part of application No. 09/878,158, filed on Jun. 8, 2001, which is a continuation-in-part of application No. 09/724,985, filed on Nov. 28, 2000, which is a continuation-in-part of application No. PCT/GB99/01764, filed on Jun. 4, 1999.

(30) Foreign Application Priority Data
Jun. 5, 1998 (GB) ................. 9812227.8
Apr. 12, 1999 (GB) ................. 9908333.9

(51) Int. Cl.
C12N 5/00 (2006.01)
C12N 5/16 (2006.01)
C07K 21/08 (2006.01)
C07K 16/18 (2006.01)
C07K 1/10 (2006.01)

(52) U.S. Cl. .................. 435/325; 435/326; 435/328; 435/332; 435/334; 435/344; 435/373; 435/375; 435/377

(58) Field of Classification Search .................. None
See application file for complete search history.

(56) References Cited

U.S. PATENT DOCUMENTS 5,026,785 A 6/1991 Mage et al.
5,662,907 A * 9/1997 Kubo et al. ............... 424/185.1
6,475,483 B1 * 11/2002 Steinman et al. .......... 424/93.7
6,548,067 B1 * 4/2003 Seeman et al. ............ 424/192.1

FOREIGN PATENT DOCUMENTS

| EP | 0 352 761 A | 1/1990 |
|---|---|---|
| WO | WO95/04817 A1 * | 2/1995 |
| WO | WO96/04314 A1 | 2/1996 |
| WO | WO97/24446 A2 | 7/1997 |
| WO | WO99/11775 A1 | 3/1999 |
| WO | WO99/13095 A2 | 3/1999 |
| WO | WO99/64464 A2 | 12/1999 |

OTHER PUBLICATIONS

Ferrari et al. J. Immunol. 2004. vol. 173, pp. 2126-2133.*
Dannenberg et al. Abstract of J. Clin. Oncol. 2005. vol. 23, No. 2, pp. 254-266.*
Xing et al. Embase accession # 2005266079 Abstract of Chinese J. Clinical Rehabilitation. 2005. vol. 9, pp. 151-153.*
Moro et al. Cancer Res. 57: 1922-1928, 1997.*
Huang, J.H. et al., "Protein transfer of preformed MHC-peptide complexes sensitizes target cells to T cell cytolysis," *Immunity*, 1(7): 607-13, 1994.
Moris, A. et al., "Cutting Edge: Characterization of Allorestricted and Peptide-Selective Alloreactive T Cells Using HLA-Tetramer Selection", *The Journal of Immunology*, 166: 4818-4821, 2001.
Ogg, G.S. et al., "Sensitization of tumor cells to lysis by virus-specific CTL using antibody-target MHC class I/peptide complexes," *British Journal of Cancer*, 82(5): 1058-62, 2000.
Sadovnikova, E. et al., "Generation of human tumor-reactive cytotoxic T cells against peptides presented by non-self HLA class I molecules", *Eur. J. Immunol.*, 28: 193-200, 1998.

* cited by examiner

Primary Examiner—Christina Chan
Assistant Examiner—Marianne DiBrino
(74) Attorney, Agent, or Firm—Frommer Lawrence & Haug LLP; Thomas J. Kowalski; Angela M. Collison

(57) ABSTRACT

A complex including an HLA class I molecule and attaching means for selectively attaching the HLA class I molecule to a target is disclosed, and a method is provided for producing or enhancing an immunological response against a target cell, by attaching said complex to the target cell. Where the target cell is diseased, foreign, or malignant cell, this method may be used to promote lysis of the target cell by T cells in the immune system. Where the target cell is an antigen presenting cell, this method may be used to promote proliferation of specific T cell clones. Uses include prevention and treatment of diseases including cancer, leukaemia, infectious diseases, viral infections, such as HIV, bacterial infections, such as tuberculosis, and parasitic infections such as malaria.

7 Claims, 21 Drawing Sheets

Expression of B9E9 sfvScSA targeted HLA-A2/M1 complexes on HLA class I −ve B cells. Detected with FITC-W6/32

Cr Release assay from PBLs stimulated with B9E9 sfvScSA targeted HLA-A2/M1

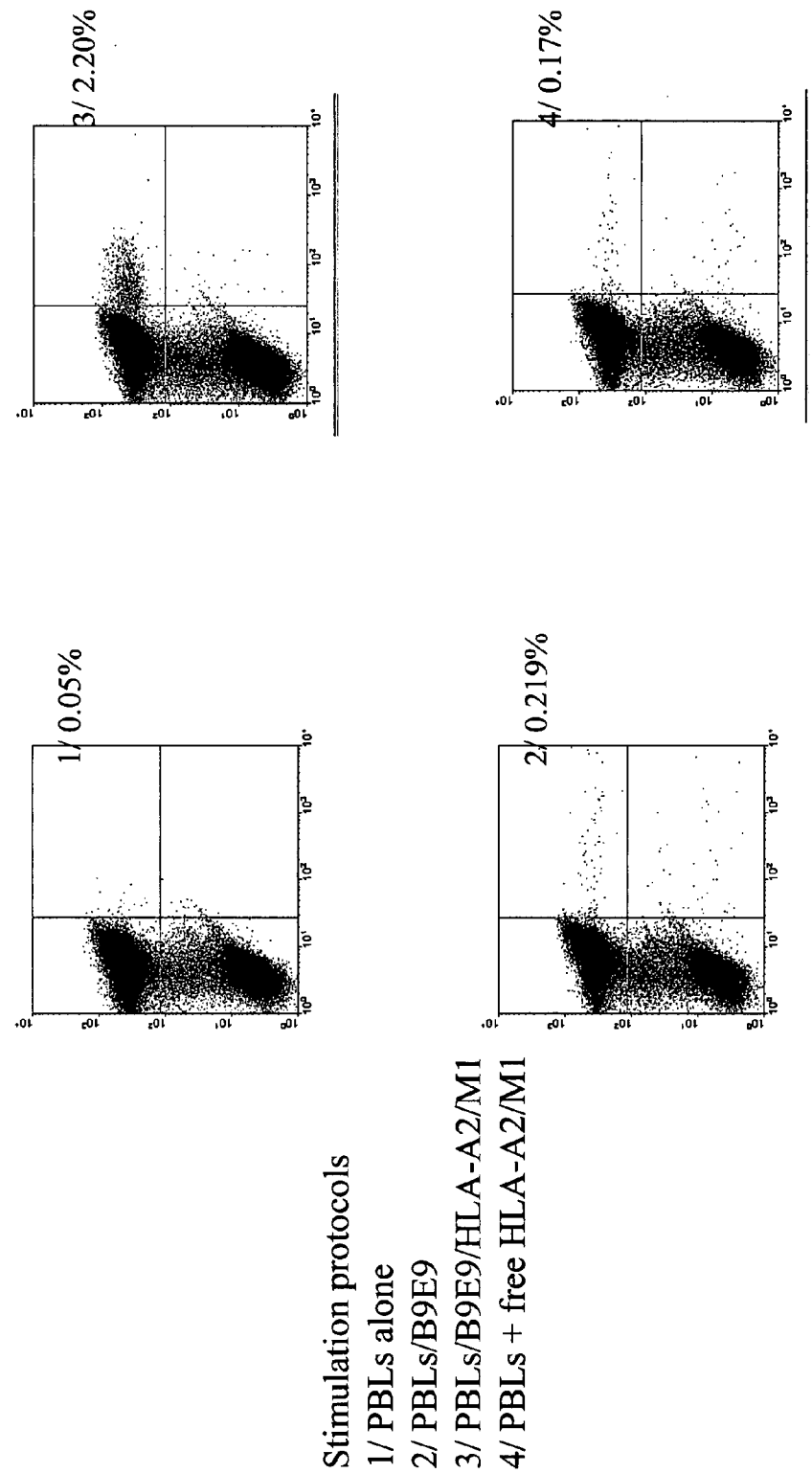

Cr Release assay from PBLs stimulated with B9E9 sfvScSA targeted HLA-A2/BMLF1

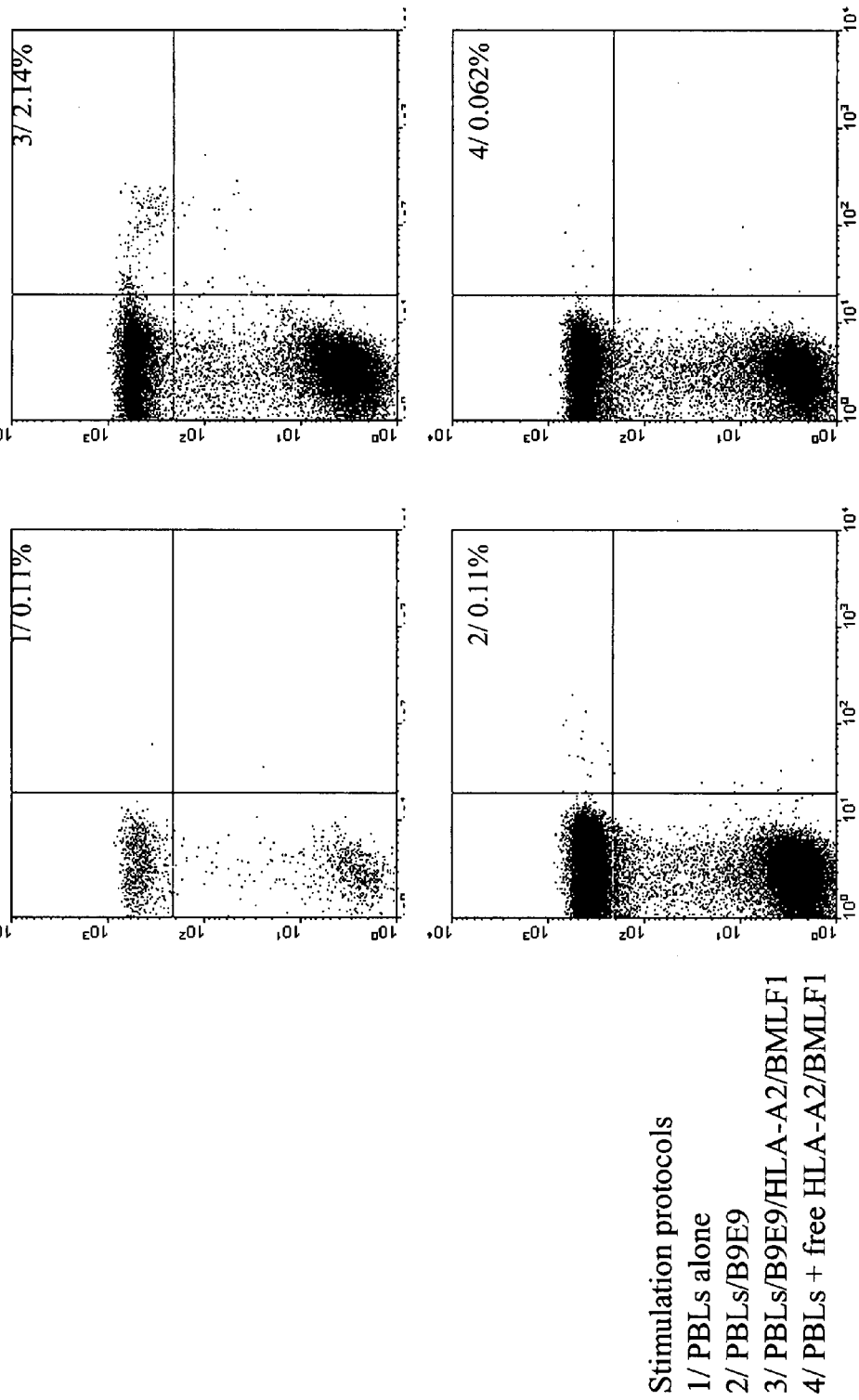
FIGURE 11D  CD8/Tetramer staining from PBLs stimulated with B9E9 sfvScSA targeted HLA-A2/BMLF1
Stimulation protocols
1/ PBLs alone
2/ PBLs/B9E9
3/ PBLs/B9E9/HLA-A2/BMLF1
4/ PBLs + free HLA-A2/BMLF1

Tetramer demonstration of the specificity of CTL induction with B9E9 sfvScSA targeted HLA-A2/peptide complexes

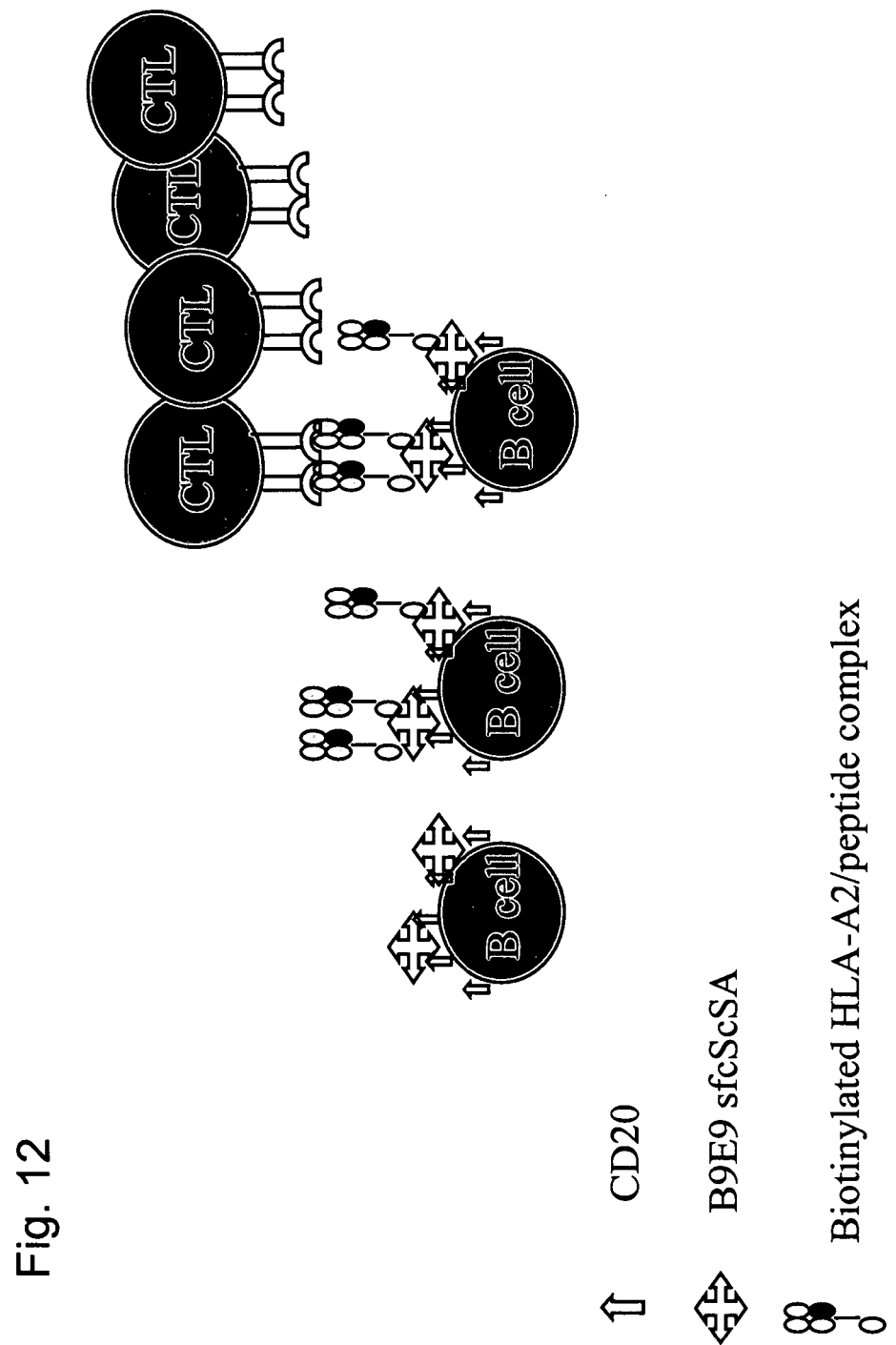

SEQUENCE LISTING

```
<160> NUMBER OF SEQ ID NOS: 6

<210> SEQ ID NO 1
<211> LENGTH: 8
<212> TYPE: PRT
<213> ORGANISM: Epstein-Barr virus

<400> SEQUENCE: 1

Arg Ala Lys Phe Phe Gln Leu Leu
1               5

<210> SEQ ID NO 2
<211> LENGTH: 9
<212> TYPE: PRT
<213> ORGANISM: Homo sapiens

<400> SEQUENCE: 2

Ser Leu Tyr Asn Thr Val Ala Thr Leu
1               5

<210> SEQ ID NO 3
<211> LENGTH: 10
<212> TYPE: PRT
<213> ORGANISM: Homo sapiens

<400> SEQUENCE: 3
```

```
Glu Ala Ala Gly Ile Gly Ile Leu Thr Val
1               5                   10

<210> SEQ ID NO 4
<211> LENGTH: 9
<212> TYPE: PRT
<213> ORGANISM: Influenza virus

<400> SEQUENCE: 4

Gly Ile Leu Gly Phe Val Phe Thr Leu
1               5

<210> SEQ ID NO 5
<211> LENGTH: 9
<212> TYPE: PRT
<213> ORGANISM: Epstein-Barr virus

<400> SEQUENCE: 5

Gly Leu Cys Thr Leu Val Ala Met Leu
1               5

<210> SEQ ID NO 6
<211> LENGTH: 10
<212> TYPE: PRT
<213> ORGANISM: Homo sapiens

<400> SEQUENCE: 6

Glu Leu Ala Gly Ile Gly Ile Leu Thr Val
1               5                   10
```

METHOD FOR PRODUCING OR ENHANCING A T-CELL RESPONSE AGAINST A TARGET CELL USING A COMPLEX COMPRISING AN HLA CLASS I MOLECULE AND AN ATTACHING MEANS

RELATED APPLICATIONS

This application is a continuation-in-part of U.S. application Ser. No. 09/878,158, filed Jun. 8, 2001 which is a continuation-in-part of U.S. application Ser. No. 09/724,985, filed Nov. 28, 2000 as the continuation-in-part of PCT/GB99/01764, filed Jun. 4, 1999, designating the U.S. and published as WO 99/64464, with claims of priority from Great Britain application nos. 9812227.8, filed Jun. 5, 1998 and 9908333.9 filed Apr. 12, 1999. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

BACKGROUND

Cytotoxic T cells in the cellular immune system are responsible for recognising cells that display "foreign" markings, and triggering an immunological response against such cells. Each cytotoxic T cell expresses a number of cell surface recognition receptors, which recognition receptors all possess precise specificity for a particular "foreign" peptide sequence, which recognition receptors are adapted to bind to HLA class I molecules expressed on the surface of cells scanned by the T cell. HLA class I molecules are cell surface molecules which possess a peptide binding groove exposed on the external surface of the cell, which groove is arranged under normal circumstances to bind a peptide derived from the interior of the cell. When a recognition receptor on a cytotoxic T cell binds to an HLA class I molecule on the surface of a scanned cell, the recognition receptor is enabled to contact the peptide binding groove of the HLA class I molecule and interact with any peptide contained therein. If this peptide matches the specificity of the recognition receptor, the T cell is said to recognise the scanned cell, and may consequently trigger an immunological response against said scanned cell.

Cytotoxic T cells of various specificities within a host immune system are also able to recognise and trigger an immunological response against a cell exhibiting an HLA class I molecule which is of a different allotype from the HLA class I molecules of the host cells. An immunological response of this kind is known as an "alloreactive" response.

An immunological response against a cell usually results in the lysis of the cell and/or the local release of cytokines. It has however been observed that cytotoxic T cells do not trigger the lysis of so-called antigen presenting cells (APCs) in this way. Instead, the immunological response triggered by T cell recognition of an HLA class I molecule on the surface of an antigen presenting cell results in the direct selective proliferation of the cytotoxic T cell. The host immune system consequently becomes immunised against any cells exhibiting the foreign peptide recognised by the surface recognition receptors on this T cell.

It is recognised that the effector mechanisms of the cellular immune system could be a powerful tool in the prevention and treatment of many illnesses, including malignant processes and infectious and auto-immune diseases, including cancer. A small number of the HLA class I molecules on a tumour cell surface may be found to bind peptides which are selectively expressed or over-expressed in tumour cells and are capable of being recognised by cytotoxic T cells in the immune system. Such peptides may furthermore be tumour specific, being found only infrequently, or not at all, on the HLA class I molecules of non-tumour cells. An example of one such tumour specific peptide is the HMW-MAA antigen found on melanoma cells. However, the number of HLA molecules presenting such peptides is generally too small to stimulate an effective immunological response against the tumour cell. Moreover, such peptides are rarely, if ever, presented by HLA class I molecules on the surface of APCs.

Attempts to enhance the response of the cellular immune system to tumour cells have hitherto focused on increasing tumour cell immunogenicity. In particular, various efforts have been made to produce high-level expression of immunogenic HLA class I molecules on the surface of tumour cells, through the techniques of gene therapy. The delivery of cDNA encoding an HLA class I gene containing an immunogenic peptide in the leader sequence of the HLA molecule has been described in Kang (Cancer Res. 57, 1997, 202-205). Meanwhile, Stopeck (J Clinical Oncolosv 15, 1997, 341-349) describes the transfection of allogeneic HLA class I in patients with melanoma. This work has demonstrated some response in clinical trials, but has also highlighted the difficulties involved in targeting tumour cells at multiple sites in vivo through the techniques of gene therapy.

FIELD AND SUMMARY OF THE INVENTION

In a broad aspect, the invention relates to the targeting of HLA class I peptide complexes via a monoclonal antibody delivery system to tumour cells. This has the effect of redirecting pre-existing T cell specificities, for example T cells with viral specificity, to kill tumour cells targeted with the HLA class I/peptide complexes.

In another broad aspect, the invention relates to targeting of HLA class I peptide complexes via a monoclonal antibody delivery system to an antigen presenting cell. This produces an immune response, e.g. to activate and expand a CTL response to make sufficient cells to allow them to have an action against distant cells expressing this same combination of HLA class I molecule and peptide. In one embodiment, the invention relates to 'immunising' with combination(s) of a HLA class I molecule plus peptide that could be tumour related such as Mart 1, Mage or other suitable molecule(s).

FURTHER SUMMARY ASPECTS OF THE INVENTION

In a first further aspect, the present invention provides a complex comprising an HLA class I molecule or fragment thereof, the HLA class I molecule or fragment thereof comprising:

(i) a T cell binding portion; and (ii) attachment means for selectively attaching the HLA class I molecule or fragment thereof to a target cell;

wherein the HLA class I molecule or fragment thereof binds or is attached to a recognition peptide, wherein the recognition peptide is arranged to be presented by said HLA class I molecule or fragment thereof for T cell recognition, wherein the attachment means comprises:

(a) a linking polypeptide with specific affinity for a molecule on the surface of the target cell (b) a coupling system for coupling the linking polypeptide to the HLA class I molecule or fragment thereof.

The coupling system may comprise:

a first small molecule joined to the linking polypeptide; and a second small molecule joined to the HLA class I molecule, wherein interaction of the small molecules forms a stable bridge between the linking polypeptide and the HLA class I molecule.

The coupling system may comprise a three-step chain of small molecules.

The coupling system may comprise biotin and avidin/streptavidin.

The coupling system may comprise calmodulin and calmodulin binding peptide.

The recognition peptide may comprise a peptide which elicits a strong cytotoxic T cell response or which is capable of inducing a powerful immune response.

The recognition peptide may comprise one or more of a tumour specific peptide, a viral peptide, a bacterial peptide, or a parasitic peptide.

The recognition peptide may comprise a peptide selected from the group consisting of an influenza virus peptide, a measles virus peptide, an Epstein-Barr virus peptide, an Epstein-Barr virus peptide, a peptide comprising the RAKFFQLL epitope (SEQ ID NO: 1) of the lytic protein BZLF1, a Cytomegalovirus peptide and a tetanus toxoid peptide.

The linking polypeptide may comprise an antibody or a fragment thereof.

The antibody may be a monoclonal antibody.

The attaching means may specifically bind to a molecule on the surface of an antigen presenting cell.

In a second further aspect, the present invention provides a complex comprising (i) a HLA class I molecule or a fragment thereof;

(ii) an attachment means comprising either a) a molecule which specifically binds a polypeptide selected from the group consisting of carcinoembryonic antigen, placental alkaline phosphatase, polymorphic epithelial mucin, human chorionic gonadotrophin, CD20, prostate specific antigen, ca-125 and HMW-MAA; or b) an antibody selected from the group consisting of C46, 85A12, H17E2, HMFG1, W14, 1F5, 225.28s;

(iii) a recognition peptide selected from the group consisting of an influenza virus peptide, a measles virus peptide, an Epstein-Barr virus peptide, an Epstein-Barr virus peptide, a peptide comprising the RAKFFQLL epitope (SEQ ID NO: 1) of the lytic protein BZLF1, a Cytomegalovirus peptide and a tetanus toxoid peptide;

wherein the recognition peptide is arranged to be presented by the HLA class I molecule or fragment thereof for T cell recognition.

The complex may comprise a coupling system for joining the attachment means to the HLA molecule or fragment thereof.

The coupling system may comprise one or more of biotin, avidin, streptavidin, calmodulin or calmodulin binding protein.

In a third further aspect, the present invention provides a complex comprising (i) a HLA-A2 molecule or a fragment thereof, conjugated to biotin (ii) a monoclonal antibody 225.28s conjugated to biotin (iii) avidin (iv) a peptide comprising the amino acid sequence SLYNTVATL (SEQ ID NO: 2).

In a fourth further aspect, the present invention provides a method for attaching a complex according to the present invention to a target cell, comprising the step of contacting the target cell with the HLA class I molecule or fragment thereof and the attaching means.

In a fifth further aspect, the present invention provides a method for producing or enhancing an immunological response against a target cell, comprising the step of attaching a complex according to the present invention to the target cell.

In a sixth further aspect, the present invention provides a pharmaceutical composition comprising (i) a complex according to the present invention, and (ii) a pharmaceutically acceptable excipient or carrier.

In a sixth further aspect, the present invention provides the use of a complex according to the present invention in the preparation of a medicament for induction of a cytotoxic T cell response against a cell recognised by the attachment means.

In a seventh further aspect, the present invention provides the use of a complex according to the present invention in the preparation of a medicament for immunising a subject against said recognition peptide.

In an eighth further aspect, the present invention provides a kit comprising one or more pharmaceutical compositions according to the present invention and written instructions for the administration of said composition(s) to a subject.

In a ninth further aspect, the present invention provides a method for directing a cytotoxic T cell response against a target cell, the method substantially as described herein with reference to FIG. 1.

In a tenth further aspect, the present invention provides a method for producing an immune response against a peptide, the method substantially as described herein with reference to FIG. 4.

In an eleventh further aspect, the present invention provides a method of treating a blood sample, preferably an isolated blood sample, wherein said method comprises forming in said blood sample and/or adding to said blood sample a complex accoding to the present invention.

BRIEF DESCRIPTION OF THE DRAWINGS

FIG. 10 shows a FACs analysis of the time course of binding of HLA-A2/M1 peptide complexes to HLA class I –ve cells (Daudi) via an antibody bridge. (Detected with an FITC conjugated anti-MHC monoclonal antibody (W6/32) (this antibody recognises HLA class I that is conformationally correct) (Ancell Ltd)

FIGS. 11A-11E. Shows a bar chart, four scatterplots, a further barchart, four further scatterplots, and six further scatterplots. In more detail, FIG. 11 illustrates the result of a Tetramer FACs analysis of the cells cultured from peripheral blood cells incubated with or without the anti-CD20 B9E9-streptavidin fusion protein and HLA-A2/M1 peptide complex. The cells are dual stained with a FITC conjugated monoclonal antibody to CD8 and a PE conjugated HLA-A2 tetramer with specificity for HLA-A2/MI. FIG. 11 further shows the results of Tetramer FACs analysis of the cells cultured from PBLs incubated with either the anti-CD20 B9E9-streptavidin fusion protein alone (sample C) or the anti-CD20 B9E9-streptavidin fusion protein plus either the HLA-A2/MI peptide complex (sample F) or the HLA-A2/BMLF1 peptide complex (sample I). Cells from these samples were then dual stained with a FITC conjugated monoclonal antibody to CD8 and a PE conjugated HLA-A2 tetramer with specificity for HLA-A2/MI or HLA-A2/BMLF1 as indicated.

FIG. 12. Shows schematic representation of the two-step targeting system delivering HLA-class I peptide complexes to the surface of B cells. Step 1 is the delivery of the anti-CD20 B9E9 sfvScSA fusion protein. Step 2 the delivery of recombinant biotinylated HLA class I peptide. These steps are followed by the selective proliferation of peptide specific CTLs.

DETAILED DESCRIPTION AND EXAMPLES

Figure 1:
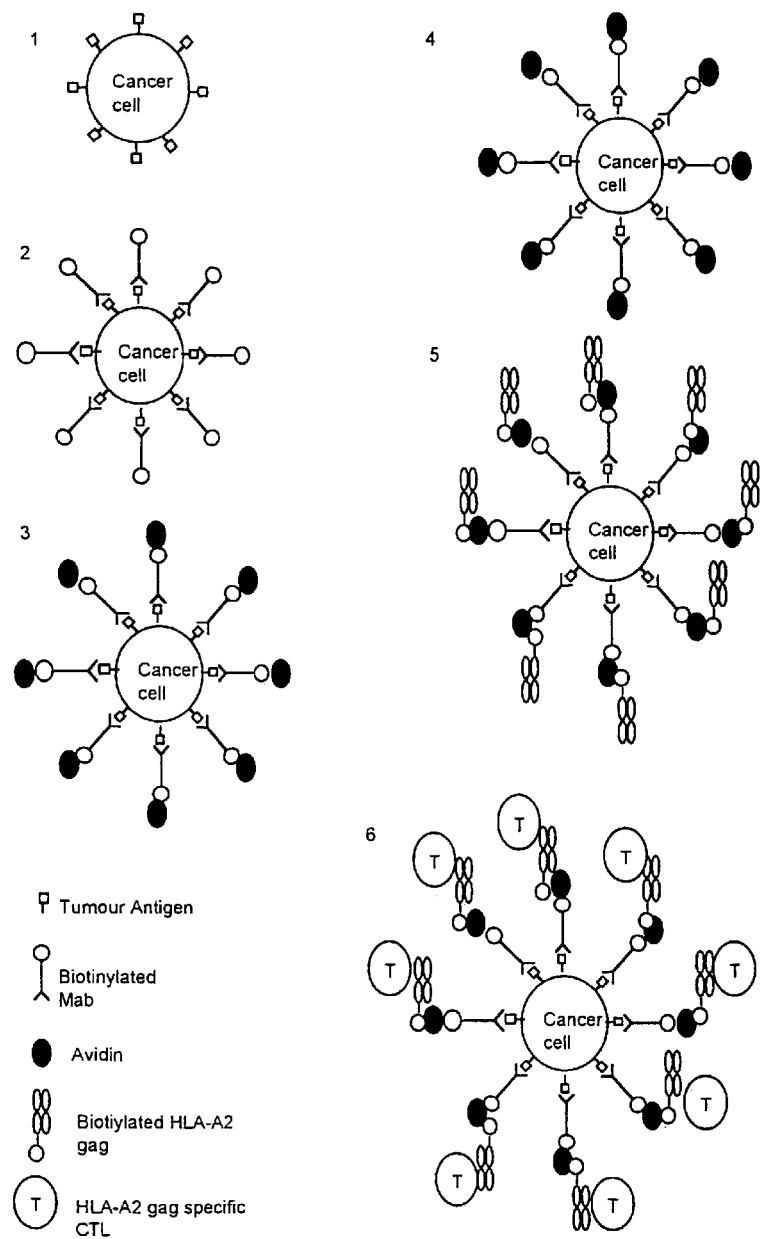
FIG. 1 shows a diagram showing the method/idea for delivering HLA molecules to the surface of tumour cells.

As is explained herein and in predecessor applications, U.S. application Ser. No. 09/724,985, filed Nov. 28, 2000, PCT/GB99/01764, filed Jun. 4, 1999, designating the U.S. and published as WO 99/64464, and Great Britain application nos. 9812227.8, filed Jun. 5, 1998 and 9908333.9 filed Apr. 12, 1999, incorporated herein by reference, antibody targeted HLA class I/peptide complexes have clear clinical value. The teachings and disclosure in the predecessor applications pertain to the present invention, and thus, attention is respectfully directed to the text of those applications, as the entire text of the predecessor applications are incorporated herein by reference as if they were set out in full.

The present application sets out to provide improved means for producing or enhancing an immunological response against a target cell, and to provide an improved method for treating or preventing cancer and other malignant, infectious or auto-immune diseases.

Accordingly, in one aspect of the present invention there is provided a complex comprising an HLA class I molecule or fragment thereof, which HLA class I molecule or fragment thereof comprises a T cell binding portion, and attaching means for selectively attaching said HLA class I molecule or fragment thereof to a target cell, characterized in that said HLA class I molecule or fragment thereof binds or is attached to a recognition peptide, which recognition peptide is arranged to be presented by said HLA class I molecule or fragment thereof.

In another aspect of the present invention there is provided a method of attaching an HLA class I molecule or fragment thereof to a target cell, which HLA class I molecule or fragment thereof comprises a T cell binding portion, comprising the step of introducing to said target cell said HLA class I molecule or fragment thereof and attaching means for selectively attaching said HLA class I molecule or fragment thereof to the target cell.

In yet another aspect of the present invention, there is provided a pharmaceutical composition comprising an HLA class I molecule or fragment thereof, which HLA class I molecule or fragment thereof comprises a T cell binding portion; attaching means for selectively attaching said HLA class I molecule or fragment thereof to a target cell; and an appropriate excipient or carrier.

The HLA class I molecule or fragment thereof may bind a peptide, which peptide is arranged to be presented for T cell recognition by said HLA class I molecule or fragment thereof. Said peptide may be attached to the HLA class molecule or fragment thereof in accordance with the method described in Garboczi (*PNAS* 89, 1992, 3429-3433).

The attaching means preferably comprises a linking polypeptide with high specific affinity for a target cell specific molecule on the surface of the target cell. By "target cell specific molecule" herein is meant any molecule that is characteristically expressed or over-expressed on the surface of the target cell. By way of example, in cancer cells said "target cell specific molecule" could include any of the following tumour associated antigens: carcinoembryonic antigen, placental alkaline phosphatase, polymorphic epithelial mucin, human chorionic gonadotrophin, CD20, prostate specific antigen, ca-125, HMW-MAA and others.

Conveniently, the linking polypeptide will comprise an antibody, preferably a monoclonal antibody, raised against said target cell specific molecule (Riethmuller and Johnson, *Curr. Opin. Immunol.* 4, 1992, 647-655). Suitable antibodies for this purpose include C46, 85A12, H17E2, HMFG1, W14, 1F5, 225.28s (Buraggi 1985 *Cancer Res.* 45. 3378-3387), and others. Deposits of the immortalised hybrids producing these antibodies have been made at the American Type Culture Collection, Rockville Md., USA. Further examples of antibodies are described in Maloney et al (*Blood* 84, 1994, 2457-2466), Riethmuiler et al (*Lancet* 343, 1994, 1177-1183) and Hird et al (*Br. J. Cancer* 68, 1993, 403-406).

Said linking polypeptide may comprise an antibody raised against a target cell specific molecule and a coupling system for coupling said antibody to said HLA class I molecule or fragment thereof. The coupling system may comprise a two- or three-step chain of well-characterised paired small molecules, joined to the antibody and the HLA class I molecule so as to form a stable bridge between the two. Examples of paired small molecules which might be used in this connection include (but are not limited to) biotin and avidin/streptavidin (Moro, 1997 *Cancer Res.* 57, 1922-1928; Altman et al, *Science* 274, 1996, 9496), and calmodulin and calmodulin binding peptides (Neri, 1996, *J. Invest. Dermatol.* 107, 164-170). Alternatively, said linking polypeptide may comprise an antibody-raised against a target cell specific molecule, which. antibody is adapted to be attached directly to said HLA class I molecule or fragment thereof.

In a further possible embodiment of the invention, said complex may comprise a recombinant protein, which recombinant protein includes a moiety comprising said HLA class I molecule or fragment thereof, and a moiety comprising said attaching means.

The HLA class I molecule or fragment thereof may be purified from plasma or platelets or made recombinantly. The HLA class I molecule or fragment thereof may further be arranged to bind and present for T cell recognition a defined peptide of choice, such as a viral, bacterial, parasitic, or tumour-specific peptide. Attachment of the HLA class I molecule or fragment thereof to the target cell may be achieved by introducing said HLA class I molecule or fragment thereof and said attaching means to the vicinity of the target cell. The target cell may be a culture cell in vitro, but will advantageously be in the body of a patient. Preferably, the target cell will be arranged to be contacted by a cytotoxic T cell, which cytotoxic T cell is adapted to recognise said HLA class I molecule or fragment thereof either as being of a mismatched allotype or as binding a foreign peptide, and which cytotoxic T cell is capable of triggering an immunological response against said target cell.

In one embodiment of the present invention the target cell is of a type which may be lysed as a result of an immunological response thereagainst. Advantageously, the target cell is a tumour cell or any diseased or foreign cell the presence of which is undesired in a patient, such as a cancer cell, leukaemia cell, a cell infected with the HIV virus or with any other microbe or virus, a cell responsible for detrimental activity in auto-immune disease, and so on. In order to accelerate the triggering of an immunological response against said target cell in a patient, said HLA class I molecule or fragment thereof will preferably be capable of producing a powerful immune response from the cellular immune system of the patient. Accordingly, said HLA class I molecule or fragment thereof may bind a viral or microbial peptide, preferably a viral or microbial peptide to which the patient is likely to have had previous exposure. In particular, said HLA class I molecule or fragment thereof may bind an influenza virus peptide, a measles virus peptide, an Epstein-Barr virus peptide, in particular an Epstein-Barr virus peptide comprising the RAKFFQLL epitope (SEQ ID NO: 1) of the lytic protein BZLFI, a Cytomegalovirus peptide, or a tetanus toxoid peptide. Alternatively, said HLA class I molecule or fragment thereof may bind any peptide which already has a strong cytotoxic T cell response or which is capable of inducing a powerful immune response. The allotype of said HLA class I molecule or fragment thereof may additionally be different from the allotype of the HLA class I molecules of the patient, so that an alloreactive response may additionally be triggered against said target cell.

In another embodiment of the invention the target cell is an antigen presenting cell (APC). Recognition by a cytotoxic T cell of an HLA class I molecule or fragment thereof attached to said APC may result in direct and selective proliferation of the cytotoxic T cell. Accordingly, said HLA class I molecule or fragment thereof will advantageously be adapted to present for T cell recognition a tumour specific peptide as defined above, or a viral peptide, or a bacterial peptide, or a parasitic peptide, or any peptide which is exclusively or characteristically presented by HLA class I molecules on the surface of diseased, malignant or foreign cells the presence of which is undesirable in a patient. Peptides linked to malignant conditions have been characterised (Brossart, 1998 *Cancer Res.* 58. 732-736 and Lucas, 1998 *Cancer Res.* 58, 743752), as have peptides of parasitic origin (Khusmith, 1991 *Science* 252, 715718). The attachment of an HLA class I molecule or fragment thereof to an APC, in accordance with the present invention, may be used for in vivo immunisation against cells presenting a given peptide, or ex vivo production of cytotoxic T cells of a particular specificity.

Where the target cell is a tumour cell or microbially infected cell, the pharmaceutical composition of the present invention may be used for the treatment of a tumour or microbial disease respectively, and there is provided a method of treating a tumour or microbial disease in a patient, comprising the step of administering to a patient in need thereof an effective amount of said pharmaceutical composition.

It must be noted that whilst many tumour types express tumour associated antigens, heterogeneity in the level of expression does occur, so some tumour cells may not be targeted by antibody and lysed directly. However, in vitro date from the analogous antibody-superantigen system shows that the high local levels of cytokines released by activated T cells can lead to the death of untargeted bystander tumour cells (Dohlsten et al, *Int. J. Cancer* 54, 1993, 482488). It is likely that similar effects will occur in a targeting system using MHC class I/peptide complexes. Similarly, it is possible that the presence of activated cytotoxic T cells releasing cytokines in the tumour may lead to enhancement of a specific anti-tumour immune response. Where the target cell is an APC and the HLA class I molecule or fragment thereof binds a tumour-specific peptide or any peptide which is exclusively or characteristically presented by HLA class I molecules on the surface of a virally, bacterially, parasitically or microbially infected cell, the pharmaceutical composition of the present invention may be used for immunising against the tumour or viral, bacterial, parasitic or microbial infection respectively, and there is provided a method of immunising against a tumour or viral, bacterial, parasitic or microbial infection in a patient, comprising the step of administering to a patient in need thereof an effective amount of said pharmaceutical composition.

The response of said patient may be improved by in vivo cytokine support, or by the infusion of antigen-specific cytotoxic T cells expanded ex vivo. Transient immunosuppression (Ledermann at al, *Int. J. Cancer* 47, 1991, 659664) may be used to minimise the immunogenic response of a patient to components of the targeting system such as the avidin bridge. The administration of said pharmaceutical composition may be by way of oral, sublingual, transdermal or parenteral administration.

Said effective amount of the pharmaceutical composition will depend on factors such as the nature and severity of the disorder being treated and on the weight, age and condition of the patient.

Pharmaceutical Compositions

The present invention also provides a pharmaceutical composition comprising a therapeutically effective amount of the complex(es) of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the composition is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, the complex(es) of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The complex(es) of the present invention may be prepared in situ in the subject being treated. In this respect, nucleotide sequences encoding said complex(es) or parts thereof may be delivered by use of non-viral techniques (e.g. by use of liposomes) and/or viral techniques (e.g. by use of retroviral vectors) such that the said complex(es) are expressed from said nucleotide sequence(s).

In a preferred embodiment, the pharmaceutical of the present invention is administered topically.

Hence, preferably the pharmaceutical is in a form that is suitable for topical delivery.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components of the present invention may be administered alone but will generally be administered as a pharmaceutical composition—e.g. when the components are is in admixture with a suitable pharmaceutical excipient, diluent or carrier selected with regard to the intended route of administration and standard pharmaceutical practice.

For example, the components can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the complex(es) may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of:

oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

In a preferred aspect, the pharmaceutical composition is delivered topically.

It is to be understood that not all of the components of the pharmaceutical need be administered by the same route. Likewise, if the composition comprises more than one active component, then those components may be administered by different routes.

If a component of the present invention is administered parenterally, then examples of such administration include one or more of: intravenously, intra-arterially, intraperitoneally, intrathecally, intraventricularly, intraurethrally, intrastemally, intracranially, intramuscularly or subcutaneously administering the component; and/or by using infusion techniques.

For parenteral administration, the component is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the component(s) of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the complex(es) and a suitable powder base such as lactose or starch.

Alternatively, the component(s) of the present invention can be administered in the form of a suppository or pessary, or it may be applied topically in the form of a gel, hydrogel, lotion, solution, cream, ointment or dusting powder. The component(s) of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the component(s) of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending upon the need, the complex(es) may be administered at a dose of from 0.001 to 30 mg/kg body weight, such as from 0.1 to 10 mg/kg, more preferably from 0.1 to 1 mg/kg body weight.

Formulation

The component(s) of the present invention may be formulated into a pharmaceutical composition, such as by mixing with one or more of a suitable carrier, diluent or excipient, by using techniques that are known in the art.

Pharmaceutically Active Salt

The complex(es) of the present invention may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Treatment

It is to be appreciated that all references herein to treatment include one or more of curative, palliative and prophylactic treatment. Preferably, the term treatment includes at least curative treatment and/or prophylactic treatment.

The treatment may be of one or more of cancer, tumour or related complaint. Treatment may be for producing/enhancing/augmenting immune response(s) in malignant illnesses such as cancer/leukaemia/lymphoma. Furthermore, treatment may be for infectious diseases including HIV and leprosy.

Therapy

The complex(es) of the present invention may be used as therapeutic agents—i.e. in therapy applications.

As with the term "treatment", the term "therapy" includes curative effects, alleviation effects, and prophylactic effects.

The therapy may be on humans or animals.

EXAMPLES

The invention shall be further described in the following examples.

Example 1

The following components were used:

| | |
|---|---|
| Target cells: | A human melanoma cell line Mel 1, deposited at the Department of Immunology, Institute of Molecular Medicine, Oxford, that carries the HLA class I allotype HLA-A2. The cell line was grown in standard RPMI tissue culture media. A human melanoma cell line Mel 2, deposited at the Department of Immunology, Institute of Molecular Medicine, Oxford, that does not carry the HLA class I allotype HLA-A2. The cell line was grown in standard RPM1 tissue culture media. |
| Attaching means: | A monoclonal antibody 225.28s (Buraggi 1985 Cancer Res. 45 3378-3387) that binds to the HMW-MAA antigen on human melanoma cells. Biotin is chemically conjugated onto this antibody as described in Bayer 1990, Methods Embryology 184, 138-160. Pure hen egg avidin obtained commercially from Societa Prodotti Antibiotics, Milan, Italy. |
| HLA: | Biotin conjugated recombinant HLA class I allotype HLA-A2 molecules, as described in Altman 1996, Science 274, 94-96, further containing the "gag" peptide that is part of the HIV virus. This peptide comprises the amino acid sequence -SLYNTVATL- (SEQ ID NO:2). Methods for the preparation/isolation thereof are described in Johnson 1991, J Immunol 147, 1512. The "gag" peptide was attached to the HLA-A2 molecules as described in Garboczi 1992, PNAS 89, 3429-3433. |
| T cells: | HLA-A2/gag specific cytotoxic T cells obtained from an A2 + ve HIV patient as described in Altman 1994, Science 274, 94-96. |

In order to establish the ability of the attaching means to cause display of the HLA class I molecules on the surface of Mel 2 target cells, approximately 200,000 cells were first incubated with biotin conjugated monoclonal antibody 225.28s at a final concentration of 20 µg/ml at 37° C. for 30 minutes. Following this the cells were washed in tissue culture media (RPMI 1640, obtainable from Gibco, Scotland). The Mel 2 cells were then incubated with avidin at a final concentration of 10 µg/ml for 10 minutes at 37° C. and washed in tissue culture media. Finally, the Mel 2 cells were incubated with biotin conjugated HLA class I HLA-A2/gag molecules at a final concentration of 20 µg/ml at 37° C. for 20 minutes.

Figure 2:
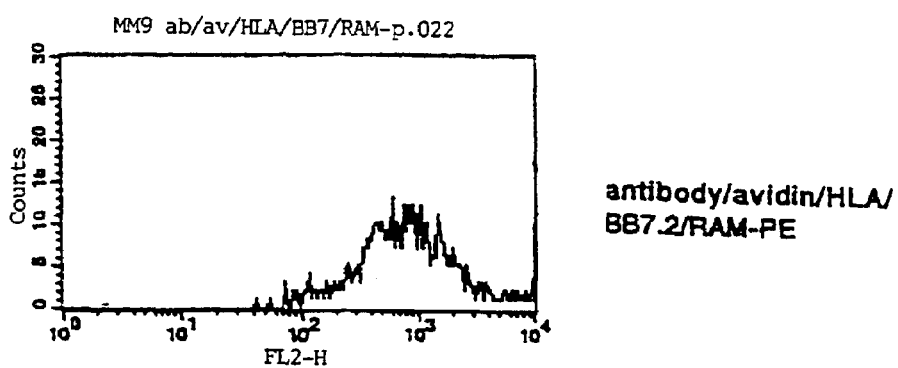
FIG. 2 shows a FACs analysis of HLA-A2−ve Mel 2 melanoma cells treated with biotin-conjugated monoclonal antibody 225.28s, avidin, biotin-conjugated HLA-A2/gag complexes, anti-HLA-A2 monoclonal antibody BB7.2 and phycoerythrin-conjugated rabbit anti-mouse antibody.

The binding of recombinant HLA-A2 to the treated Mel 2 cells was shown by the attachment of anti-HLA-A2 monoclonal antibody BB7.2 (Santos-Aguado 1988, *J. Immunol* 141, 2811-2818) following incubation with BB7.2 antibody at a final concentration of 10 µg/ml at 37° C. for 30 minutes. After washing in tissue culture media the cells were incubated with phycoerythrin conjugated rabbit anti-mouse antibody (Sigma, Poole, UK) at a final concentration of 10 µg/ml for 30 minutes at 37° C. and analysed in a Becton Dickson Facscan machine. The result of this analysis is shown in FIG. 2 which demonstrates a positive signal indicating the presence of HLA-A2 molecules attached to the surface of the Mel 2 cells.

A chromium release T cell cytotoxicity assay was then performed in order to establish the ability of HLA-A2/gag specific T cell clones to lyse Mel 1 cells coated with HLA-A2/gag in accordance with the present method. Approximately $10^6$ Mel 1 cells were first pre-incubated with 1.85 µBq $Na_2{}^{51}CrO_4$ (obtained from Amersham International, Amersham, UK) for 1 hour at 37° C. The pre-incubated Mel 1 cells were then incubated with biotin conjugated monoclonal antibody 225.28s at a final concentration of 20 µg/ml at 37° C. for 30 minutes, and washed in tissue culture media. Following this, the Mel 1 cells were incubated with avidin at a final concentration of 10 µg/ml for 10 minutes at 37° C. and then washed again in tissue culture media. The Mel I cells were then incubated with biotin conjugated HLA class I HLA-A2/gag molecules at a final concentration of 20 µg/ml at 37° C. for 20 minutes and washed with tissue culture media.

Having been coated with HLA class I HLA-A2/gag, the chromium-treated Mel I cells were then incubated with HLA-A2/gag specific cytotoxic T cells in ratios of 0:1 to 20:1 of effector to target cells at 37° C. for 20 hours. Lysis of Mel I cells treated with $Na_2{}^{51}CrO_4$ results in the release of radioactive chromium, which may be detected by analysis in a scintillation counter. In order to establish the percentage of Mel 1 cells lysed following incubation with HLA-A2/gag specific cytotoxic T cells, the following measurements were taken: background release of chromium from the Mel I cells in media alone ("M"); release of chromium from the Mel 1 cells following incubation with the T cells ("E"); release of chromium from the Mel 1 cells following final treatment with 5%/o Triton X-100 detergent ("T"). Treatment with detergent will cause the lysis of all the remaining intact Mel 1 cells.

% Mel 1 lysis by cytotoxic T cells was calculated as follows:

$$\% \text{ lysis} = 100 \times \frac{(E-M)}{(T-M)}$$

This analysis was carried out on Mel 1 cells treated with biotin-conjugated 225.28s, avidin, and biotin-conjugated HLA-A2/gag. As a control, the analysis was also carried out on Mel 1 cells treated with biotin-conjugated 225.28s and avidin alone, and on Mel 1 cells treated with avidin and biotin-conjugated HLA-A2/gag alone.

Figure 3:
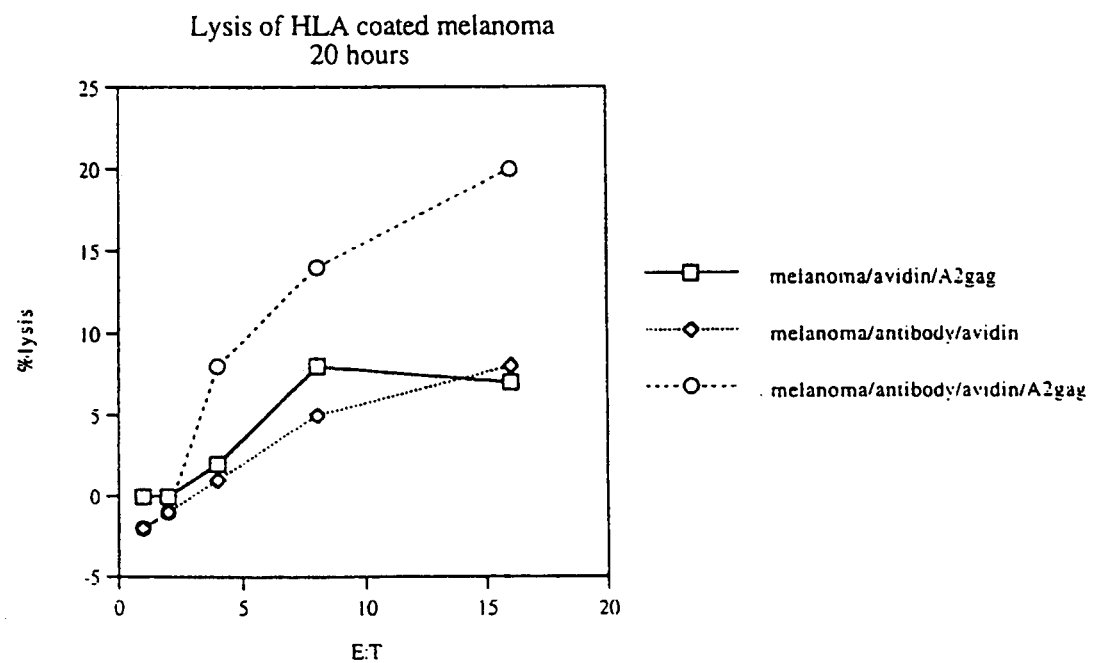
FIG. 3 shows the results of a T cell cytotoxicity chromium release assay with Mel I cells treated with the delivery system of biotin-conjugated monoclonal antibody 225.28s, avidin, and biotin-conjugated HLA-A2/gag complexes. These cells were incubated with HLA-A2/gag specific cytotoxic T cells with effector/target ratios of 0:1-20:1 for 20 hours.

The key results of this analysis are illustrated in FIG. 3, which indicates that significant lysis (20%) of Mel 1 cells by HLA-A2/gag specific cytotoxic T cells occurs only when the Mel 1 cells have been treated with all the components of the attaching and delivery means of the present invention (ie biotin-conjugated 225.28s monoclonal antibodies, avidin, and biotin-conjugated HLA-A2/gag). No significant increase in cell lysis over background levels was observed in either of the control runs.

Example 2

The following components were used:

| | |
|---|---|
| Target cells: | The Daudi B cell line (MHC class I-negative) melanoma line SK-mel-29 (HLA-A2.1-positive), .221/A2 (HLA-A2.1-positive), were maintained in RPMI media with 10% fetal calf serum and antibiotics in a 37° C. incubator with 5% CO2. |
| Attaching means: | Monoclonal antibodies 225.28s (Buraggi 1985 Cancer Res. 45 3378-3387) and 2147 that bind to the I-IMW-MAA antigen. Biotin is chemically conjugated onto these antibodies as described in Bayer 1990, Methods Embryology 184, 138-160. Pure hen egg avidin obtained commercially from Societa Prodotti Antibiotici, Milan, Italy. |
| HLA: | Biotinylated complexes of recombinant MHC class I and peptide were produced as described previously (Altman et al, Science 274, 1996, 94-96; Ogg et al, Science 279, 1998, 2103). Prokaryotic expression of B2M and MHC class I heavy chain, modified by the C terminal addition of a target sequence for the biotin ligase enzyme BirA, was followed by inclusion body purification. Following refolding of heavy chain and B2M around specific peptide, complexes of 45 kD were isolated by gel filtration, biotinylated overnight using BirA in the presence of ATP, Mg2+ and biotin, and then purified by gel filtration and anion exchange. |
| T cells: | Human cytotoxic T cell clones 010 (specific for HLA-A2/gag 77-85 = SLYNTVATL (SEQ ID NO:2) (Parker et al, J Immunol. 149. 1992, 3580-3587)) and IF9 (specific for HLA-A2/melan-A 26-35 = EAAGIGILTV (SEQ ID NO:3) (Romero et al, J. Immunol. 159, 1997, 2366) were maintained in media supplemented with 5% human serum and IL-2 100 IU/ml. |

The stability of the MHC class I/peptide complexes was first established by an ELISA assay. Various MHC class I/peptide complexes, including HLA-A2/Gag3Y, HLA-A2/Gag3F, HLAA2/Lmp2, HLA-B35/Env and HLA-B35/nef, were prepared as outlined above, and were pre-incubated at 10 µg/ml in tissue culture media for 0-20 hours at 37° C. ELISA plates were coated with the mAb W6/32 (5 ug/ml in carbonate buffer pH 9.6 overnight at 4° C.) which recognises conformationally correct MHC class I molecules (Parham, 1979), and then blocked by incubation in 1% bovine serum albumin for 2 hours at 37° C. The MHC class I/peptide complexes were incubated for 30 minutes with the ELISA plates at room temperature, and binding was detected with rabbit anti-human B2 microglobulin followed by alkaline phosphatase conjugated goat anti-rabbit immunoglobulin, and substrate. All incubations were separated by extensive washes in PBS.

Absorbances at 600 nm were measured in a TITERTEK™ Multiscan ELISA reader. Three assays were performed for each sample, and the mean reading was calculated.

Figure 5:
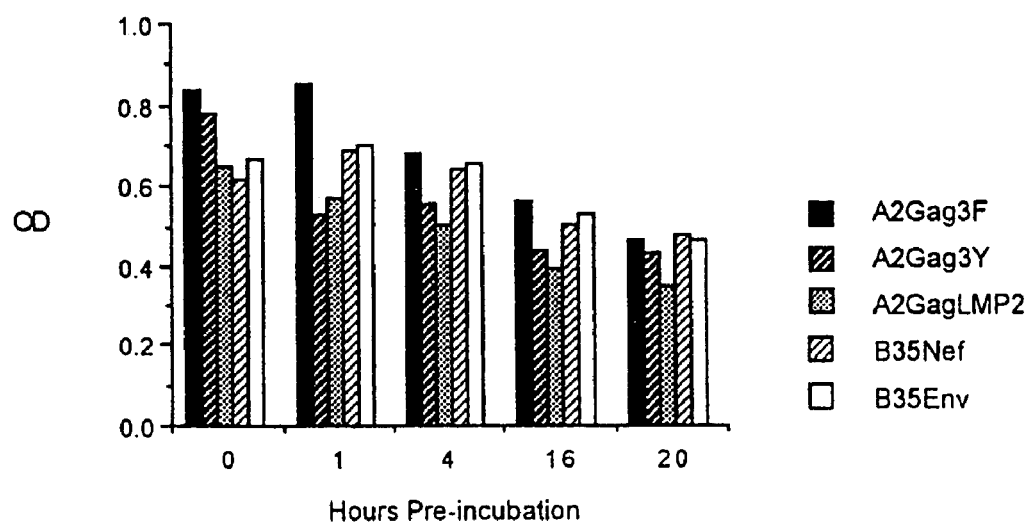
FIG. 5 shows the results of an ELISA assay, described in Example 2 below, for demonstrating the stability of various MHC class I/peptide complexes at 37° C. The results shown are the mean of assays performed on each sample in triplicate.

The results obtained with samples preincubated for 0, 1, 4, 16 and 20 hours are shown in FIG. 5. The results demonstrate that the HLA-A2/gag complexes have appreciable stability in culture media at 37° C., with an estimated half-life in excess of 24 hours.

In storage at 0.5-1 mg/ml at 4° C. HLA-A2/gag complexes appear to be stable for at least 12 months (data not shown).

To demonstrate the ability of the attaching means to cause display of MHC class I on the surface of Daudi cells, Daudi cells deficient in MHC class I were sequentially incubated at 4° C. with biotinylated anti-CD20 (Ancell, Nottingham, UK; mAb 2H7 (Berenson et al, Blood 67, 1986, 509-515) at 1 µg/ml for 30 minutes); hen egg avidin (S.P.A., Milan, Italy, at 10 µg/ml for 10 minutes); biotinylated HLA-A2/gag (at 10 µg/ml for 10 minutes); and FITC labelled anti-MHC class I (Ancell, Nottingham, UK; mAB 3FI0 (Eisenbarth et al, J. Immunol. 124, 1980,1237-1244) at 10 µg/ml). Parallel controls omitted one or other incubation. Cells were washed 3 times in PBS between stages and then fixed in PBS plus 2% formaldehyde and analysed by flow cytometry.

Figure 6:
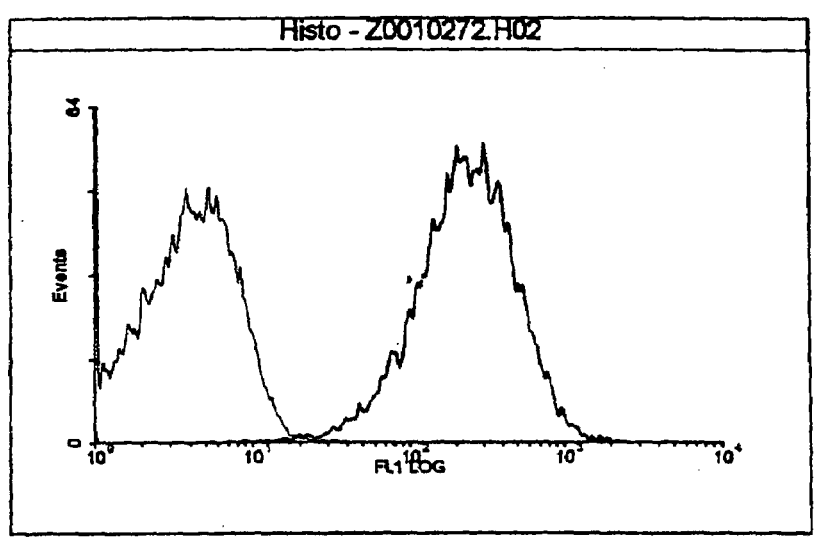
FIG. 6 shows a FACS analysis of HLA-class 1 deficient Daudi cells targeted with HLA-A2 via biotinylated anti-CD20 mAb. Trace 1 (lefthand trace) corresponds to native untargeted Daudi cells. Trace 2 (righthand trace) corresponds to Daudi cells targeted with mAb/avidin/HLA-A2/gag/FITC anti-MHC class I. Mean fluorescence trace 1=0.31, mean fluorescence trace 2=24.3 (arbitrary fluorescence units).

Cells incubated with all three layers of the labelling system had high levels of detectable MHC class I/peptide on their surface compared to untreated Daudi cells (FIG. 6). Cells treated with only any 2 components of the 3-step system gave fluorescence levels comparable to untreated cells (data not shown).

A chromium release cytotoxicity assay was carried out to establish the ability of specific T cell clones to lyse Daudi or SK-mel-29 cells in accordance with the present invention. Daudi or SK-mel-29 cells were incubated with $^{51}CrO_4$ at 2 uCi/uL for 1 hour at 37° C. and then sequentially incubated with: the biotinylated mAbs 2H7 or 225.28s (anti-HMW-MAA) respectively; avidin; and biotinylated HLA-A2/gag complexes as detailed above. Peptide pulsed target cells were incubated with gag 77-85 or melan-A 26-35 peptides at 0.1 uM for 1 hour at 37° C. After washing, labelled target cells were plated into 96-well round bottom plates at 2,500 cells per well, followed by human CTLs at various effector: target ratios. Following incubation at 37° C., 20 ul of supernatant was collected and the amount of $^{51}Cr$ released was determined. The percentage of cytotoxicity (lysis) obtained at each effector:target ratio was calculated as: 100×(E-M)/(T-M), where E=Experimental release, M=Release in media and T=Release in 5% Triton X-100 detergent.

Figure 7:
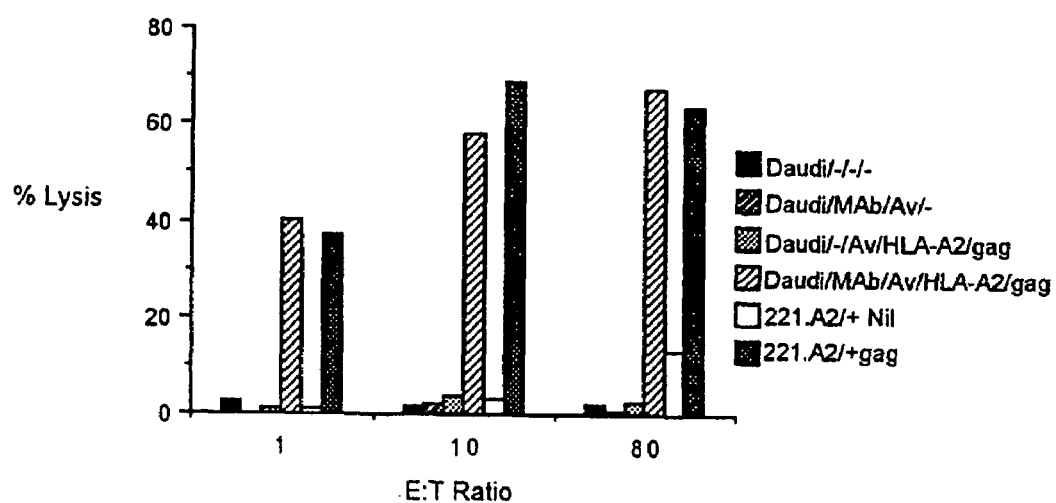
FIG. 7 shows the results of a four hour chromium release assay, described in Example 2 below, in which HLA class I-deficient Daudi cells targeted with various components of the HLA-A2/gag delivery system were incubated with HLA-A2/gag specific cytotoxic T cell clones. A comparison was made with native and peptide-pulsed 221.A2 cells (HLA-A2+ve).

The results shown in FIG. 7 are the mean of experiments performed in duplicate. As shown by these results, the CTL clone (010) efficiently lysed HLA-A2-positive targets (0.221/A2) only when these were pre-incubated with the HLA-A2/gag peptide. MHC class I-negative Daudi cells, when targeted with the HLA-A2/gag complexes of the present invention, were recognised and lysed by this CTL clone to an equivalent degree. Untargeted Daudi cells and cells targeted with only 2 of the 3 components of the targeting system were not recognised (maximal lysis <4%/a at E:T ratios of up to 80:1).

Control CTL, showing a different HLA-A2-restricted specificity (HLA-A2/melan-A), did not lyse Daudi cells targeted with the HLA-A2/gag complexes (FIG. 8), demonstrating the fine specificity of the targeting approach.

Figure 8:
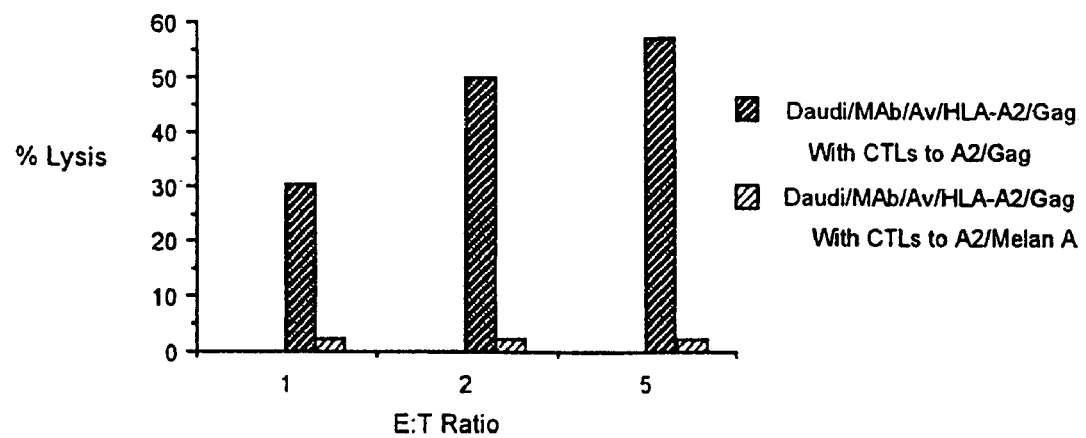
FIG. 8 shows the results of a four hour chromium release assay, described in Example 2 below, in which HLA-A2/gag targeted Daudi cells were incubated with HLA-A2/gag-specific and HLA-A2/Melan A-specific cytotoxic T cell clones.
Figure 9:
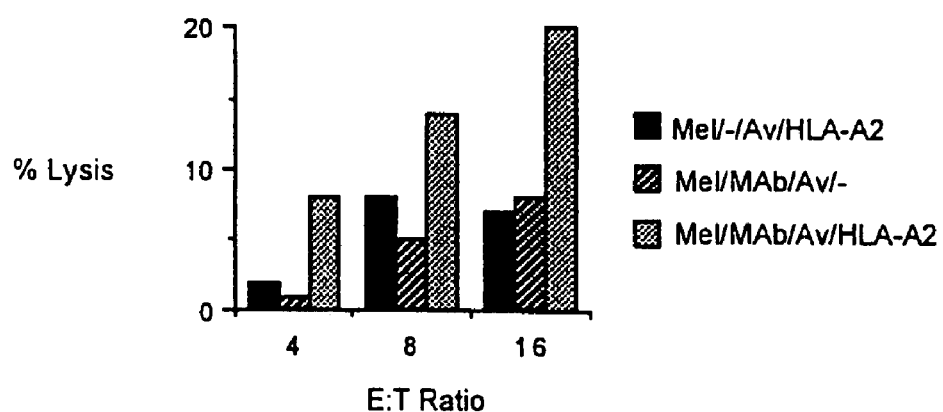
FIG. 9 shows the results of a twenty hour chromium release assay, described in Example 2 below, in which HLA-A2+ve SK29.Mel cells were incubated with HLA-A2/gag specific cytotoxic T cell clones.

Untreated Daudi cells pulsed with gag peptide alone were not lysed by clone 010 (data not shown), in keeping with their lack of endogenous MHC class I. The ability of antibody-directed HLA-A2/gag complexes to sensitise the melanoma cell line SK-mel29 to lysis by HLA-A2/gag-specific CTL line is shown in FIG. 8. At all E:T ratios, melanoma cells targeted by complexes linked to surface proteins were lysed substantially more than controls exposed to only two components of the 3-step targeting system. Additionally, MM9 melanoma cells that do not express HLA-A2 were also lysed in a similar manner (data not shown).

Example 3

Immunization/vaccination of a subject using HLA classI/peptide complex(es) to produce and/or amplify immune response(s) directed at particular cell surface molecule(s) may be accomplished according to the present invention. The immune response(s) thus produced are preferably directed at tumour cells which comprise the particular cell surface molecule(s) to which the immune response is produced. The form of this response is influenced by the particular HLA class I/peptide complex(es) used in the immunisation procedure(s).

In this example, use of antibody targeted HLA class I/peptide complexes to amplify a specific CTL response is demonstrated. Thus, example 3 also encompasses a method for delivering HLA class I/peptide complexes to the surface of antigen presenting cells.

In brief, it is demonstrated that biotinylated HLA-A2/peptide complexes immobilised on the surface of an antigen presenting cell via an antibody bridge cause the activation, amplification and expansion of cytotoxic T cells (CD8+ve) reactive with this specific HLA class I/peptide combination.

Figures for Example 3

Figure 10:
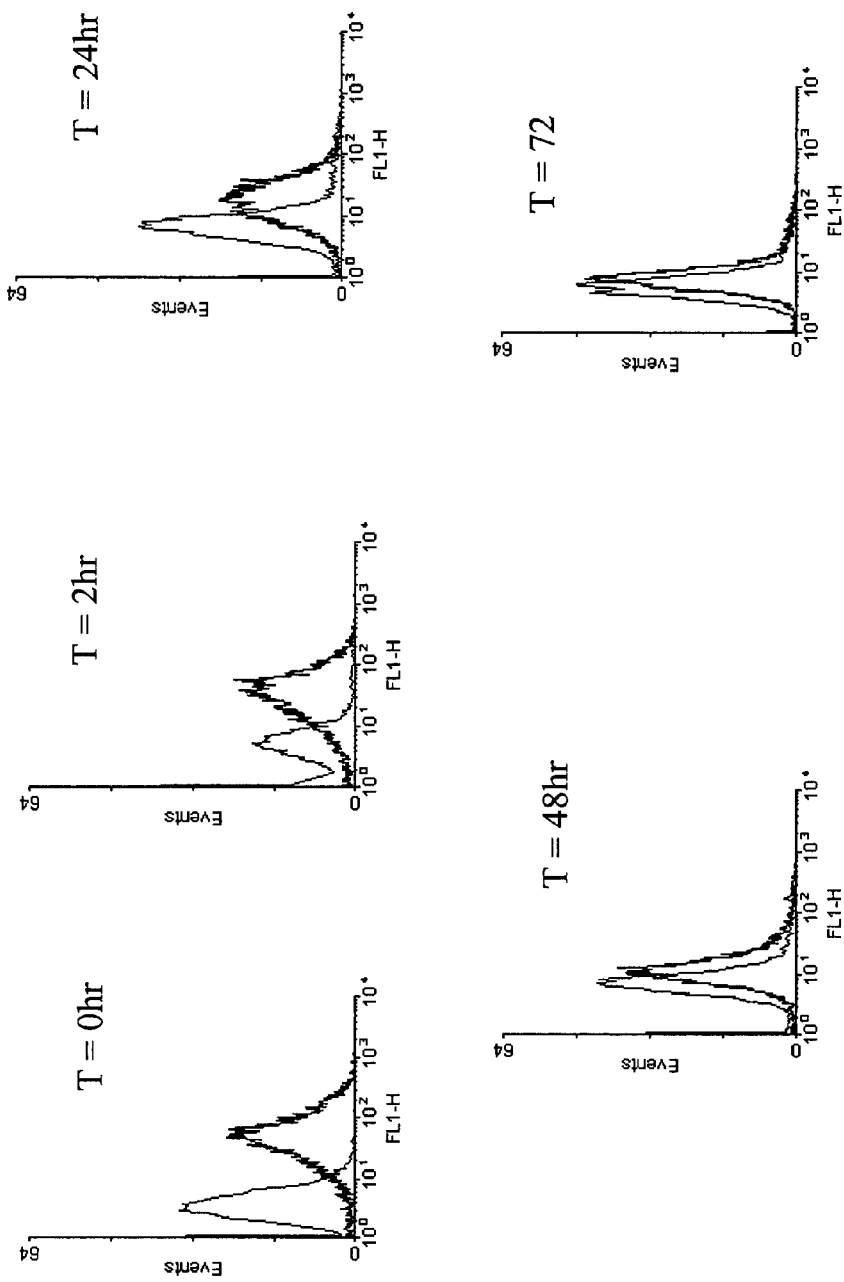
FIG. 10. Shows 5 graphs. In more detail.

FIG. 10. Shows 5 graphs. In more detail, FIG. 10 shows a FACs analysis of the time course of binding of HLA-A2/M1 peptide complexes to HLA class I –ve cells (Daudi) via an antibody bridge. (Detected with an FITC conjugated anti-MHC monoclonal antibody (W6/32) (this antibody recognises HLA class I that is conformationally correct) (Ancell Ltd)

Figure 11A:
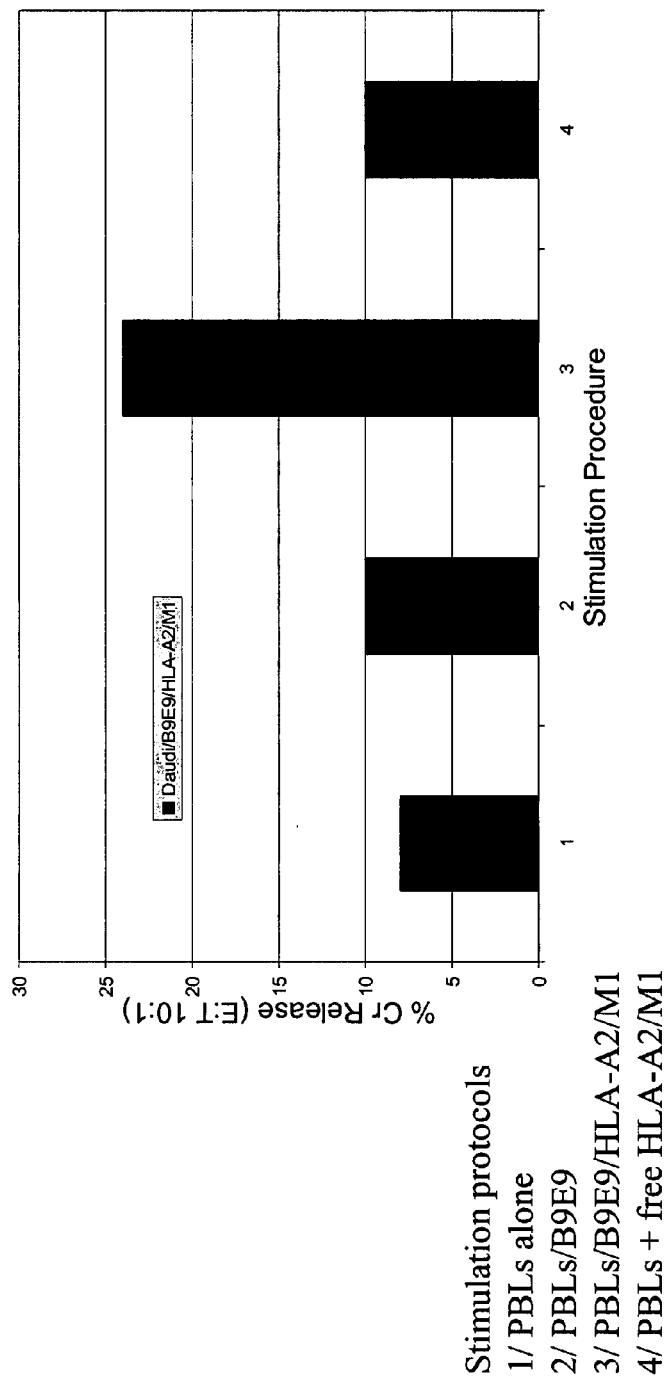
Figure 11C:
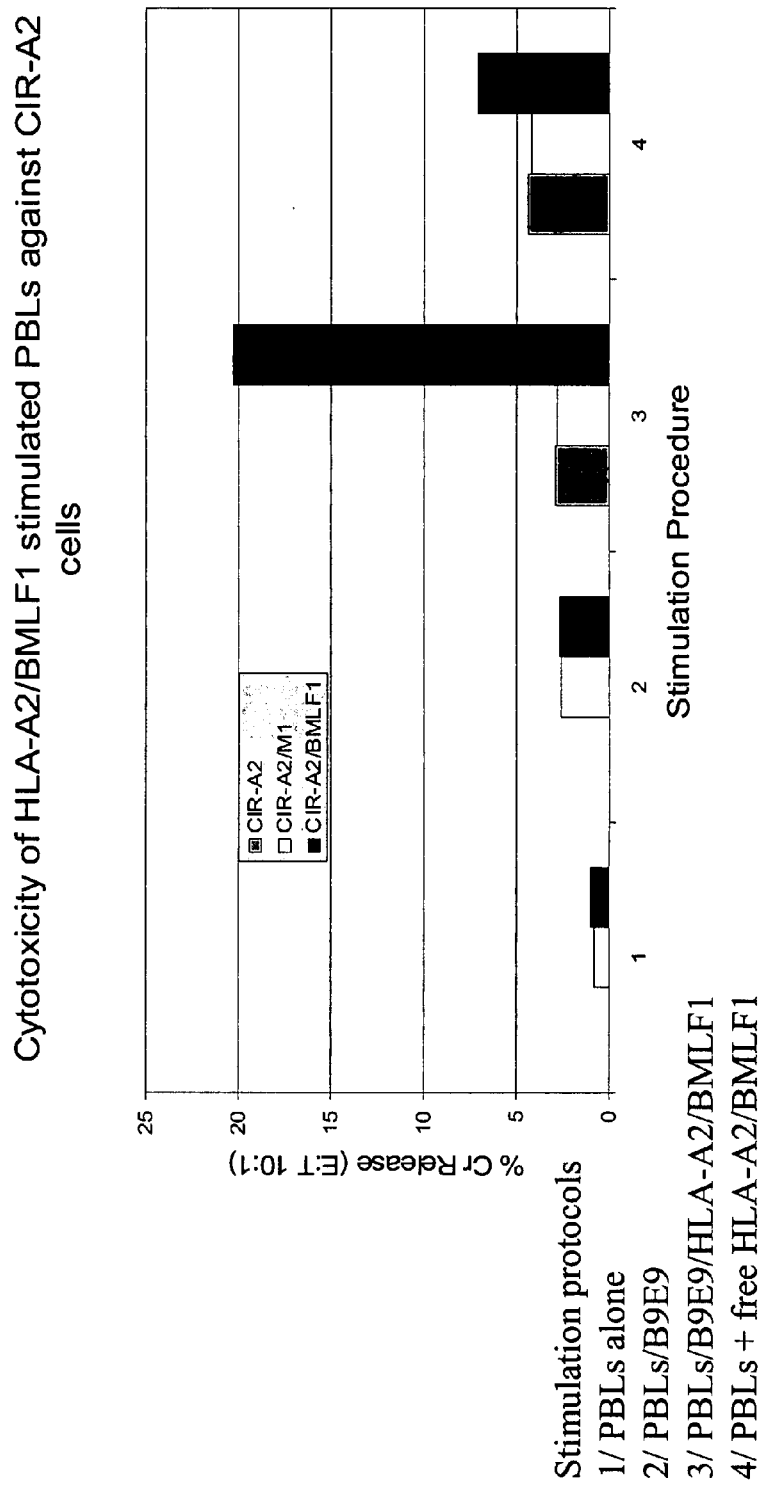
Figure 11E:
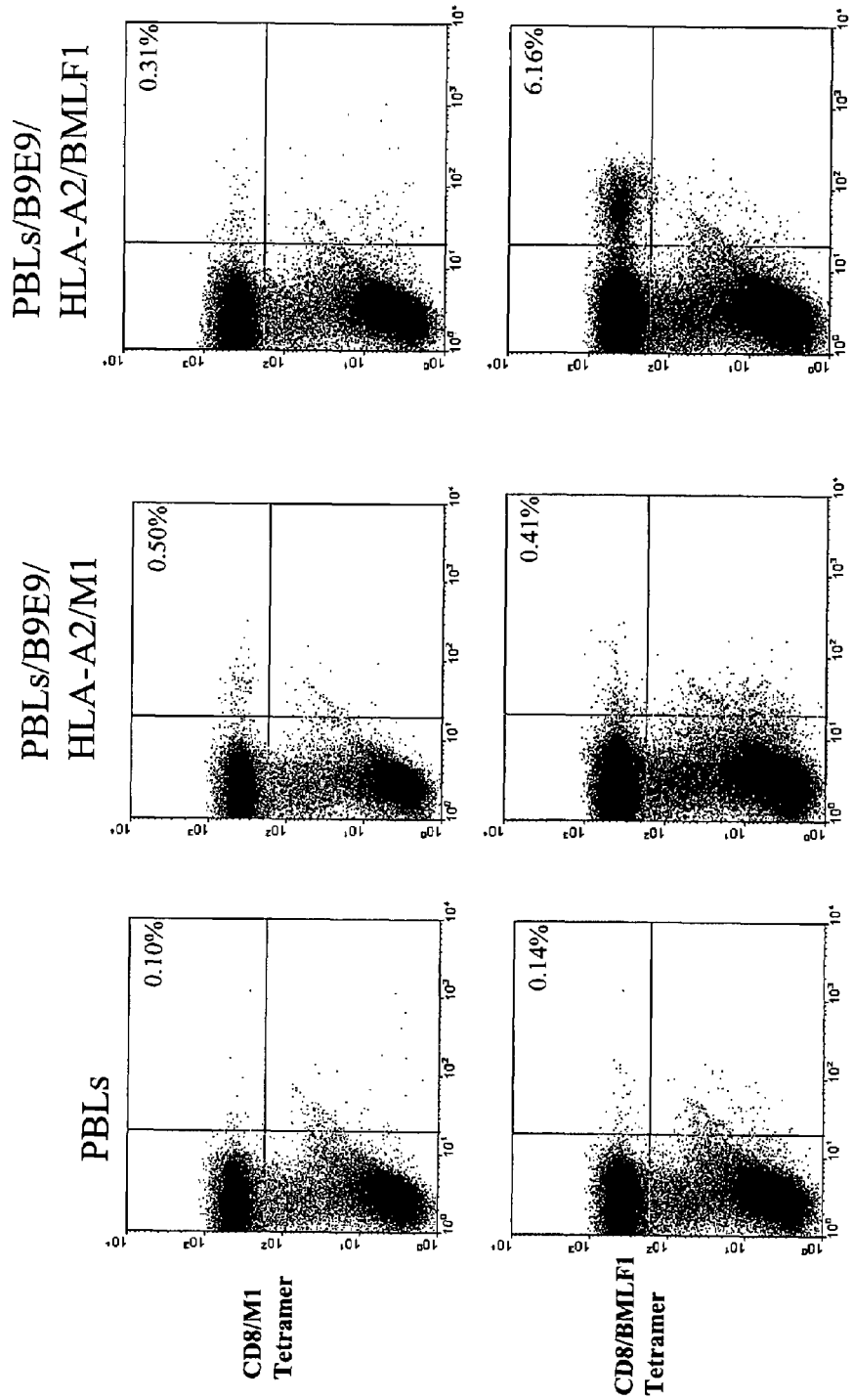

FIG. 11. Shows a bar chart, four scatterplots, a further barchart, four further scatterplots, and six further scatterplots. In more detail, FIG. 11 illustrates the result of a Tetramer FACs analysis of the cells cultured from peripheral blood cells incubated with or without the anti-CD20 B9E9-streptavidin fusion protein and HLA-A2/M1 peptide complex. The cells are dual stained with a FITC conjugated monoclonal antibody to CD8 and a PE conjugated HLA-A2 tetramer with specificity for HLA-A2/MI. FIG. 11 further shows the results of Tetramer FACs analysis of the cells cultured from PBLs incubated with either the anti-CD20 B9E9-streptavidin fusion protein alone (sample C) or the anti-CD20 B9E9-streptavidin fusion protein plus either the HLA-A2/MI peptide complex (sample F) or the HLA-A2/BMLF1 peptide complex (sample I). Cells from these samples were then dual stained with a FITC conjugated monoclonal antibody to CD8 and a PE conjugated HLA-A2 tetramer with specificity for HLA-A2/MI or HLA-A2/BMLF1 as indicated.

Table 1 (EX3): Shows the results of a T cell chromium release assay using HLA class I negative Daudi B cell lymphoma cells as targets. These cells were coated with HLA-A2/M1 peptide complexes attached via the anti-CD20 B9E9-streptavidin fusion protein.

Table 2(EX3): Shows the results of a T cell chromium release assay using CIR-A2 target cells that had been 'pulsed' with either nothing or the flu M1 or EBV BMLF1 peptides as indicated. The effector cells were cultured from peripheral blood cells, of an HLA-A2+ve healthy donor, incubated with the anti-CD20 B9E9-streptavidin fusion protein alone and HLA-A2/M1 or HLA-A2/BMLF1complexes.

Materials and Methods for Example 3

The Following Components were Used

Cells: Daudi cells. A human B cell lymphoma line derived from a patient with Burkitts lymphoma. The cell line was grown in RPMI standard tissue culture media.

Peripheral Blood Cells: Peripheral blood mononuclear cells from a donor previously demonstrated to be HLA-A2. These cells were separated from whole blood by differential centrifugation using Ficoll Hypaque and cultured in standard RPMI tissue culture media.

C1R-A2 cells: An HLA class I negative, human B cell line transfected with the gene for HLA-A2. These cells were cultured in RPMI tissue culture media supplemented with G418 400 ug/ml.

Attaching means: B9E9-streptavidin fusion protein, a tetrameric recombinant monoclonal antibody that binds to the B cell antigen CD20 (Schultz et al Cancer Research 2000).

HLA class I/peptide complexes: Biotin conjugated recombinant HLA class I allotype HLA-A2 molecules as described by (Altman 1996 (Science 274, 94-96)) These complexes can contain the choice of immunogenic peptides including the influenza matrix MI or EBV BMLF 1 peptides. The complexes were obtained from ProInmune Ltd Oxford England.

Experimental Procedures:FACs Analysis:

Methods:

1/Confirmation of ability to target HLA-A2/M1 peptide complexes to surface of B cells.

To confirm the ability of this system to target HLA-A2/M1 peptide complexes to the surface of B cells that can act as APCs, the HLA class I deficient Daudi B cell lymphoma line was used.

Approximately 1 million Daudi cells were first incubated with B9E9-SA diluted to 10 ug/ml in PBS for 1 hr at room temperature.

Following this the cells were washed twice in PBS and then incubated with biotinylated HLA-A2/MI diluted to 1 ng/ml in PBS for 1 hr at room temperature.

The cells were then washed and placed back in a small tissue culture flask containing 5 mls of RPMI and incubated at 37° C. in a 5% $CO_2$ atmosphere.

The binding and time course of the residence of recombinant HLA-A2 on the cell surface of the targeted Daudi cells was demonstrated by FACs analysis.

At various time points treated Daudi cells were removed, washed in PBS and incubated for 30 minutes at room temperature with an FITC labelled anti-HLA class I monoclonal (Ancell Ltd) antibody diluted to 10 ug/ml in PBS.

After washing in PBS the cells were analysed on a Becton Dickinson FACscan machine.

2/In vitro Immunisation Procedure.

30 mls of whole blood was obtained from a healthy volunteer (previously documented by tissue typing to be HLA-A2+ve). Peripheral blood mononuclear cells were isolated by centrifugation using Ficoll-Hypaque.

Cells were then washed in PBS and then incubated with the B9E9 anti-CD20 streptavidin fusion protein at 10 ug/ml for 1 hr at room temperature.

The cells were then washed in PBS×2, and then incubated with the HLA-A2/peptide combination of choice at a concentration of 0.5 ug/ml for 1 hr at room temperature.

After a further wash in PBS the cells were placed in to 24 well plates at 2×10$^6$ cells per well cultured in RPMI+10% FCS (heat inactivated)

On day 1 IL-7 was added to a concentration of 20 ng/ml. On day 4 and every subsequent 3 days IL-2 was added to a concentration of 10 U/ml.

The cells were incubated in a 37° C. incubator with 5% $CO_2$ for the duration of the experiment.

Various controls were also set up using this method including;
PBMCs alone,
PBMCs with the B9E9 antibody,
PBMCs without the B9E9 antibody but with free HLA-A2/peptide complex.

3/Measurement of the Induction/Amplification of CTL Activity.

The effect of the in vitro immunisation procedure on inducing the expansion of specific cytotoxic lymphocytes was assessed by two different modalities. The functional chromium release assay and the more recently described use of fluorogenic HLA class I tetramers that specifically stain cells with the desired T cell receptor specificity.

a/ Fluorogenic HLA class I Tetramer assay.

Samples from these same cells were analysed by tetramer assay.

In brief, 3×10$^5$ cells were washed in PBS and then re-suspended in 100 uL of PBS. 1 uL of an HLA-A2/peptide tetramer (ProImmune, Oxford England) was added per sample and incubated for 1 hr at room temperature.

The cells were then washed in PBS and then incubated at room temperature for 1 hr with a FITC conjugated monoclonal antibody to CD8. (Dako)

After further washing in PBS the cells were fixed in a 1% solution of formaldehyde in PBS and analysed on a Becton Dickinson FACscan machine.

The results are shown in FIG. 11.

b/ The $^{51}$Cr Release Assay.

This assay follows standard laboratory methods. In brief CIR-A2 cells were labelled with radioactive Chromium (2 uCi/ml) by incubation for 1 hr at 37° C. in a solution of $^{51}$Cr (Amersham)

The cells were then washed and then 'pulsed' with a choice of immunogenic peptides at a concentration of 20 uM or no peptide at all for the negative controls.

Alternatively Daudi lymphoma cells were used as target cells. Daudi cells were coated with HLA-A2/M1 monomers by first incubating with the B9E9-streptavidin fusion protein (10 ug/ml) for 1 hr at room temperature. After washing in PBS biotinylated HLA-A2/M1 peptide complexes were added at 1 ng/ml and then incubated for 1 hr at room temperature. Following further washing the cells were used as targets in the CTL assay.

These cells were then added to round bottom 96 well plates and various numbers of the cells produced form the 'in vitro immunization' procedure added to give the required 'effector:target' ratios.

After incubation for 4 hours at 37° C., 50 uL of the supernatant was removed and the amount of $^{51}$Cr released from lysed CIR-A2 or Daudi cells was estimated using a scintillation counter.

The results are shown in Tables 1 (EX3) and 2(EX3).

Results And Discussion

1/Demonstration of the Binding and Prolonged Residence of HLA-A2/M1 Peptide Complexes Targeted to CD20+ve Cells via the B9E9 Fusion Protein.

FIG. 10. Demonstrates the time course for the retention of the HLA-A2/M1 peptide complexes bound via the B9E9/SA fusion protein to Daudi B cells.

The results demonstrate that the binding of the HLA class I/peptide complexes via the B9E9 fusion protein results in their immobilisation on the surface of these cells.

The sequential FACs analyses demonstrate an increase in signal resulting from the bound HLA class I/peptide complexes at time 0 hrs compared to the native cells. This increase over background reduces with time but is still positive after 72 hrs incubation.

2/Demonstration by Tetramer Analysis of the Expansion of Specific CTLs Via the Binding of HLA-A2/Peptide Complexes to B Cells Via CD20

FIG. 11

Introduction

The results of the tetramer analysis are shown both in graphical (scatterplot) and numerical form. The value of the X axis varies with the degree of tetramer bind whilst the Y axis varies with the degree of binding of the monoclonal antibody to CD8. Each dot represents an individual cell that has both an X and Y value.

The cursors are set to produce cut-off values resulting in the formation of 4 quadrants.

The cells in the bottom left quadrant are judged as being negative for CD8 and tetramer binding. The cells in the left upper quadrant are positive for CD8 but negative for tetramer. The cells in the lower right quadrant are positive for tetramer but negative for CD8. The cells in the upper right quadrant are positive both for CD8 and tetramer staining, these cells are the cytotoxic T cells (CTLs) the specificity as defined by the tetramer.

1/Targeting of HLA Complexes

This experiment was performed using the HLA-A2/M1 peptide complex molecule in monomeric form for the in vitro immunization and in tetrameric form for the tetramer analysis.

Results

Sample A1

These are the results from PBMCs incubated without the B9E9 fusion protein or any biotinylated HLA-A2/peptide complexes. Here only 0.089% of all the CD8+ve cytotoxic lymphocytes in the sample have specificity for the HLA-A2/M1 tetramer.

Sample A2

These are the results from PBMCs incubated with the B9E9 fusion protein but without the addition of any biotinylated HLA-A2/M1 complexes. Here 0.0287% of all the CD8+ve cytotoxic lymphocytes in the sample have specificity for the HLA-A2/M1 tetramer.

Sample A3

These are the results from PBMCs incubated with the B9E9 fusion protein and with the addition of the biotinylated HLA-A2/M1 complexes.

Here 2.19% of all the CD8+ve cytotoxic lymphocytes in the sample have specificity for the HLA-A2/M1 tetramer.

Sample A4

These are the results from PBMCs incubated without the B9E9 fusion protein but with the addition of the biotinylated HLA-A2/M1 complexes.

Here only 0.197% of all the CD8+ve cytotoxic lymphocytes in the sample have specificity for the HLA-A2/M1 tetramer.

Further exemplary results may be found in FIG. 11.

These results show that by immobilising HLA class I/peptide complexes on to the surface of an antigen presenting cell (in this example a B lymphocyte, via a streptavin conjugated monoclonal antibody fusion protein with specificity for CD20) that a specific cytotoxic T cell response can be induced as detected by tetramer analysis.

This effect is seen when the complexes are immobilised on the cell surface—PBMCs incubated in an identical way (with IL-7 and Il-2) produce no effect (A1), neither does binding of the B9E9 fusion protein alone (A2) or the addition of free HLA class I peptide complexes (A4).

A further experiment was performed that looked at the specificity of the response to the 'in vitro immunization' procedure using two different HLA class I/peptide combinations and their respective tetramers.

2/In Vitro Immunisation Experiment

Similar in vitro immunizations of PBMCs were set up using the following combinations of the B9E9 fusion protein and HLA-A2/M1 and HLA-A2/BMLF1 complexes.

C/PBMCs with B9E9 but without any HLA-A2/peptide complex

F/PBMCs with B9E9 and with the HLA-A2/M1 complex

I/PBMCs with B9E9 and with the HLA-A2/BMLF1 complex

After 10 days incubation tetramer analysis using the anibody to CD8 and the PE conjugated tetramers HLA-A2/M1 and HLA-A2/BMLF1 were performed.

Results

The results of the dual staining were;

|  | CD8 + ve and M1 tetramer + ve | CD8 + ve and BMLF1 tetramer + ve |
|---|---|---|
| Sample C | 0.021% | 0.048% |
| Sample F | 0.254% | 0.074% |
| Sample I | 0.095% | 3.80% |

These results show that the immune response from CTLs as measured by tetramer analysis is specific to the identity of the HLA class I/peptide complex used in the 'in vitro immunization'.

In sample C which had no HLA class/peptide complex added the level of cells staining positive for CD8 and tetramer is low 0.021% for the HLA-A2/MI tetramer and 0.048% for the HLA-A2/BMLF1 tetramer.

Sample F had the HLA-A2/MI peptide complex immobilized on the B cells via B9E9 during the 'in vitro immunization' and here the level of HLA-A2/M1 tetramer positive cells has increased over 10 fold to 0.254% whilst the HLA-A2/BMLF 1 tetramer posive cells are similar to sample C at 0.074%.

The ability of the HLA-A2/BMLF1 peptide complex when immobilised on the B cells via the B9E9 fusion protein to specifically expand CTLs reactive with this peptide is shown in the results of Sample I. Here the numbers of CD8+ve cells reactive with the HLA-A2/M1 tetramer is 0.095%, which is similar to the unstimulated sample C, however now 3.80% of the CD8+ve cells bind the HLA-A2/BMLF1 tetramer, an approximately 80 fold increase in relative number.

Further exemplary results may be found in FIG. 11.

These results support the dislcosure of Experiment 1 (targeting experiment; see also predecessor applications) that the immobilised HLA class I/peptide complexes can induce a CTL response and further demonstrate that the response is specific for the HLA-classI/peptide combination. The immobilised HLA-A2/MI complex produces an expansion in CTLs that bind the HLA-A2/MI tetramer, whilst the immobilised HLA-A2/BMLF1 complex produces an expansion in CTLs that bind the HLA-A2/BMLF1 tetramer. There appears to be little non-specific activation of CTLs of the other specificity although some modest expansion may be expected due to the release of cytokines within the cell culture.

3/Demonstration by Cytotoxicity $^{51}$Chromium Release Analysis of the expansion of specific CTLs via the Binding of HLA-A2/Peptide Complexes to B cells Via CD20 According to the Present Invention.

The chromium release assay is another method for reading out T cell activity and can give information on the functional capability of CTLs. Target cells (in this case CIR-A2 or Daudi) cells are labelled with radioactive $^{51}$Chromium and then incubated with varying numbers of 'effector' cells that have been produced by the 'in vitro immunization' procedure with the PBMCs described above.

After incubation (usually 4 hours) a sample of the cell supernatant is taken and assayed for the presence of radioactive $^{51}$Cr which has been released from the target cells as a result of the action of specific cytotoxic lymphocytes in the effector cell population.

The Daudi cells do not express any HLA class I molecules on their cell surface. However if HLA class I /peptide complexes are attached to their surface via a monoclonal antibody they can serve as effective targets for CTLs (Ogg et al 2000).

The CIR-A2 cells serve as targets, they only possess one HLA class I allele the A2 molecule and the exact specifity of this can be altered by placing a peptide of choice within the peptide binding grove by 'peptide pulsing' in vitro. After performing peptide pulsing the target cells have on their cell surface of the HLA-A2 molecules a high proportion containing the peptide of choice and so form a reliable and reproducible target for CTLs of this specificity.

Targeted Lysis Experiment

The results are expressed in terms of the degree of lysis of the target cells during the $^{51}$Cr release assay.

This is calculated according to this equation; % lysis is calculated as:

$$100\% \times \frac{E - M}{T - M}$$

Where, E=experimental release

M=Media release

T=Maximal release in 5% Triton 100 The ability of the following PBMC preparations to lyse Daudi cells 'coated' with HLA-A2/M1 peptide complexes at an E;T ratio of 10:1 was;

Sample A1

These are the results from PBMCs incubated without the B9E9 fusion protein or any biotinylated HLA-A2/peptide complexes.

Sample A2

These are the results from PBMCs incubated with the B9E9 fusion protein but without the addition of any biotinylated HLA-A2/M1 complexes.

Sample A3

These are the results from PBMCs incubated with the B9E9 fusion protein and with the addition of the biotinylated HLA-A2/M1 complexes.

Sample A4

These are the results from PBMCs incubated without the B9E9 fusion protein but with the addition of the biotinylated HLA-A2/M1 complexes.

Results:Table 1 (EX3)

The % Lysis of HLA-A2/M1 Coated Daudi Cells by PBMCs Stimulated +/−HLA-A2/M1 Complexes

A1=8%
A2=10%
A3=24%
A4=10%

These results demonstrate that the treatment of PBMCs with the B9E9-streptavidin fusion protein and biotinylated HLA-A2/M1 peptide complexes in accordance with the present invention results in the amplification of the CTL response to HLA-A2/M1 as measured in this assay. PBMCs treated with both parts of the system (A3) produced 24% lysis whilst the lysis produce by untreated PBMCs (A1), or PBMCs treated with the B9E9 fusion protein alone (A2) or PBMCs treated with free HLA-A2/M1 complexes produced a maximum of only 10% lysis.

Specific Amplification Experiment

To demonstrate that the amplification of CTL response is specific to the identity of the HLA class I/peptide combination, the experiment was repeated with two HLA-A2/peptide specificities.

The results of this show differing patterns of activity for PBMCs treated with B9E9 fusion protein and the two differing HLA-A2/peptide complexes or for those treated without any HLA-A2 peptide complexes.

In this experiment CIR-A2 cells (native or peptide pulsed) were used as target cells.

The figures given are the percent lysis of peptide pulsed target cells. (E:T ratio, 5:1)

TABLE 2(EX3)

| | Immunization protocol: | | |
|---|---|---|---|
| Targets | B9E9-SA + Nil(sample C) | B9E9-SA + HLA-A2/ M1(sample F) | B9E9-SA + HLA-A2/ BMLF1(sample I) |
| CIR-A2 + Nil | 5.3% | 11.9% | 10.7% |
| CIR-A2 + M1 | 4.8% | 13.6% | 10.2% |
| CIR-A2 + BMLF1 | 7.3% | 16.4% | 23.7% |

In this experiment it is again demonstrated that PBMCs that are just targeted with the B9E9 molecule do not produce any significant lysis of target cells either native CIR-A2 or peptide pulsed with the M1 or BMLF1 peptides.

PBMCs targeted with B9E9 and HLA-A2/M1 complexes produced a weak response in this particular experiment without any clear pattern of enhanced lysis.

PBMCs targeted with B9E9 and HLA-A2/BMLF1 complexes produced CLS that had enhanced activity against CIR-A2 cells pulsed with BMLF1 (23.7%) but no increased lysis against either native CIR-A2 cells (10.7%) or CIR-A2 cells pulsed with M1 peptide (10.2%).

These results further illustrate the production of a CTL response that is predominantly against the HLA class I/peptide complex which is immobilised on the surface of the antigen presenting cell according to the present invention (in this Example, B cells via CD20 using B9E9 fusion protein).

Summary

The data in this document demonstrate that HLA-class/peptide complexes when immobilised on the surface of an antigen presenting cell via an antibody bridge result in the amplification of the immune response to that specific HLA-class/peptide complex.

The ability to specifically produce amplification of cytotoxic T cell numbers and/or activity to a particular HLA class 1/peptide combination is an advantageous feature of the present invention.

The system(s) described herein offer considerable possibilities as methods for producing/enhancing/augmenting immune response(s) in malignant illnesses such as cancer/leukaemia/lymphoma. Furthermore, these systems may find application in infectious diseases including HIV and leprosy.

Example 4

In Vivo Cancer Cell Therapy

In certain embodiments, the invention relates to using anti-viral CTLs in therapeutic approaches to combat tumour/cancer cells.

In this example, it is demonstrated that anti-viral Cytotoxic T cells inhibit the growth of cancer cells bearing antibody targeted MHC class I/peptide complexes in SCID mice.

In the present invention, cytotoxic T cells (CTLs) of non-tumour specificity are redirected against cancer cells. It is demonstrated herein that cancer cells targeted with recombinant HLA-class I/peptide complexes via an antibody delivery system can be effectively lysed by anti-viral CTLs in vitro. Furthermore, this example demonstrates effects in vivo in a mammalian system.

This system uses the recombinant anti-CD20 B9E9 sfvSCSA fusion protein to target HLA-A2/M1 complexes to CD20+ve Daudi lymphoma cells. Binding of the B9E9 sfvScSA fusion protein to Daudi cells in culture had no apparent effect on growth kinetics. Using an HLA-A2/M1 specific human T cell clone, in vitro killing of targeted Daudi cells was achieved with HLA class I concentrations as low as 5 pg/ml. A tumour protection assay using human CTL to the HLA-A2/M1 complex was performed in SCID mice. Applicant demonstrates that only 1 of 4 mice receiving Daudi cells targeted with both the B9E9 sfvSCSA fusion protein and the HLA-A2/M1 complex developed tumours, whilst in the control mice with receiving CTL but native Daudi cells 4 of 4 developed tumours, as did 4 of 4 receiving targeted Daudi cells but no CTLs.

This demonstration of the in vivo activity for the combination of targeted HLA class I/peptide complexes and anti-viral T cells, demonstrates the effectiveness of the antibody HLA class I targeting system. Clearly, this system may be advantageously combined with autologous CTLs produced by vaccination or ex vivo expansion.

This example also embraces aspects of the delivery (targeting) system. This example further illustrates a useful model system.

The B cell surface antigen CD20 serves as a good target for this system as it is expressed on many B cell malignancies, remains on the cell surface for days and is not internalised on antibody binding. Monoclonal antibodies to CD20 are available and are well characterised (Hainsworth 2000). Recombinant antibody fragments have also been developed. The tetravalent B9E9 sfvScSA fusion protein (see Schultz et al 2000) is useful as a targeting system.

To demonstrate the abilities of human CTLs of anti-viral specificity to interact with tumour cells targeted with HLA-A2/peptide complexes in a physiological setting, a model was developed as explained below.

Severe combined immunodeficient (SCID) mice are capable of supporting functional human CTLs for periods, possibly requiring a degree of cytokine support (de Kroon J. et al 1997, Buchsbaum et al 1996)

The human B cell lymphoma Daudi cell line can grow as a xenograft in SCID mice without requiring further routine immunosuppression and has been used in a variety of of therapeutic systems (see Gidlof et al 1997, Ghetie et al 1996).

This example demonstrates the in vivo interaction of human anti-viral CTLs and HLA targeted Daudi cells in a tumour protection experiment.

Cell lines:

Clone 25—A human cytotoxic T cell clone with specificity for HLA-A2/M1 was maintained in RPMI with 10% AB serum and antibiotics.

Daudi B cell lymphoma–A CD 20+ve human B cell lymphoma cell line that is deficient for the expression of HLA class I. Daudi cells were maintained in RPMI media supplemented with 10% FCS and antibiotics in a 37° C. incubator with 5% $CO_2$.

Antibodies:

Anti MHC class I (W6/32) Fitc conjugated (Sigma)

B9E9 sfvscSA. A recombinant tetravalent scFV/streptavidin fusion protein with specificity for CD20 (Schultz et al, 2000)

Mice:

Male SCID mice aged 6-8 weeks were maintained in sterile conditions in a suitable animal facility.

Facs Analysis:

Becton Dickinson FACscan machine with relevant software.

Methods:

Action of B9E9 scFvSA on Daudi cell growth

Daudi cells were washed in PBS and then incubated with dilutions of the B9E9 scFvSA in PBS for 1 hour at room temperature. After two washes the cells were re-suspended in 5 mls of tissue culture media and incubated at 37° C. in a 5% CO2 atmosphere. The proliferation of the antibody treated cells and controls was assessed by sequential counts of the viable cells using Trypan blue exclusion and a haemocytometer.

Effect of Hla Dilutions on In Vitro CTL Mediated Lysis

Standard Chromium release assays were performed using the Daudi B cell line as the target cell. Briefly, cells were labelled with 100 uCi of $^{51}Cr$ (Amersham Pharmacia) for 1 hr at 37° C. After washing in PBS, cells were incubated with B9E9 at 10 ug/ml for 1 hr at room temperature. After two further washes cells were incubated with dilutions of HLA-A2/M1 complexes in PBS for 1 hour at 4° C. After 2 further washes the cells were plated out at 3000 cells per well in U-bottomed 96 well plates. Tissue culture media, dilutions of CTLs or 5% Triton X-100 were added to a final volume of 200 uL. Plates were incubated for 4 hours at 37° C. in a 5% CO2 atmosphere and then 50 uL of supernatant collected and added to 150 uL of scintillant in a standard scintillation plate and counted.

The specific lysis was calculated as;

$$\% \text{ lysis} = \frac{\text{experimental cpm} - \text{spontaneous cpm} \times 100}{\text{maximum cpm} - \text{spontaneous cpm}}$$

The spontaneous release was measured from the cells incubated in media alone, the maximum release was measured from the cells incubated in Triton.

Facs analysis was performed on the cells targeted with B9E9 sfvScSA fusion protein and HLA-A2/M1 prepared as above. Samples of cells were washed in PBS and then incubated with FITC labelled anti-MHC class I (Ancell, Nottingham UK) and analysed by flow cytometry on a Becton Dickinson FACscan.

In Vivo Tumour Protection Assay

Healthy male SCID mice aged 6-8 weeks were used for the tumour protection assay. Four mice were used in each of the 3 groups A, B and C, treated as follows;

Group A

Mice in Group A were injected IP with $3\times10^6$ clone 25 cells in 0.2 ml of sterile PBS on Day 1. On Day 2 $1\times10^6$ Daudi cells targeted sequentially, ex vivo, with B9E9 sfvFSA (10 ug/ml) and HLA-A2/M1 (0.5 ug/ml) were injected IP in 0.2 ml of sterile PBS.

Group B

Mice in group B were injected IP with $3\times10^6$ clone 25 cells in 0.2 ml of sterile PBS on Day 1. On Day 2 $1\times10^6$ native Daudi cells were injected IP in 0.2 ml of sterile PBS.

Group C

Mice in group C were injected with 0.2 ml of sterile PBS on Day 1. On Day 2 $1\times10^6$ Daudi cells targeted sequentially, ex vivo, with B9E9 sfvFSA (10 ug/ml) and HLA-A2/M1 (0.5 ug/ml) were injected IP in 0.2 ml of sterile PBS.

The mice in all 3 groups received IP injections with human IL-2 (Chiron) 2,500 U in 0.1 ml PBS daily on days 1-3.

Following these procedures the mice were maintained in sterile conditions and monitored for tumour development. All mice were sacrificed at day 60 and assayed for tumour development.

Effects of B9E9 sfvScSA Binding on Daudi Cell Kinetics In Vitro

To investigate the possibility of any apparent effect on cell kinetics from the binding of the B9E9 sfvSA fusion protein to the Daudi lymphoma cells a simple in vitro study was performed. The results from this shown in Table 1 (EX4) show the growth over 4 days of the cells treated with dilutions of B9E9 sfvScSA and the untreated control cells. The rates of proliferation for the native and antibody bound cells appear comparable with no significant effect on the growth of the Daudi lymphoma cells in culture resulting from B9E9 sfvScSA binding.

TABLE 1(EX4)

The effects of B9E9 sfvSA binding to Daudi cell growth kinetics in vitro. (Results expressed as cells $\times 10^4$/ml)

|  | Day 0 | Day 1 | Day 2 | Day 3 | Day 4 |
|---|---|---|---|---|---|
| Expt 1 (B91E9) 19.3.01) | | | | | |
| Daudi + nil | 20 | 27 | 33 | 51 | — |
| Daudi + 0.1 ug/ml | 20 | 34 | 33 | 54 | — |
| Daudi + 1 ug/ml | 20 | 23 | 33 | 76 | — |
| Daudi + 10 ug/ml | 20 | 26 | 27 | 76 | — |
| Expt 2 (B9E9) 9.4.01) | | | | | |
| Daudi + Nil | 20 | 22 | 29 | 36 | 71 |
| Daudi +10 ug/ml | 20 | 11 | 17 | 32 | 70 |

Dose Response of HLA Binding Concentration Measured by FACs Signal and Cr Release Assay To investigate the effects of varying of the concentration of biotinylated HLA class I molecules delivered to the target cells a dose response was obtained using FACs analysis and Cr release assays as shown in Table 2(EX4).

The results indicate that a positive signal could be obtained by FACs with concentrations of biotinylated HLA down to approximately 1-5 ng/ml. The functional chromium release assay show that effective lysis of target cells can occur when exposed to concentrations of biotinylated HLA class as low as 5 pg/ml, which is producing levels of HLA binding that are significantly below the level of FACs detection.

TABLE 2(EX4)

| | Nil | 10 ug | 1 ug | 0.1 ug | 10 ng | 5 ng | 1 ng | 0.5 ng | 0.1 ng | 50 pg | 10 pg | 5 pg | 1 pg |
|---|---|---|---|---|---|---|---|---|---|---|---|---|---|
| HLA-A2/M1 complex concentration/ml | | | | | | | | | | | | | |
| FACs (Gm) | 5.8 | 18.98 | 22.54 | 18.41 | 8.47 | 7.40 | 5.71 | 5.8 | 4.6 | — | — | — | — |
| $^{51}$Cr | 2% | n/d | n/d | n/d | 42% | n/d | 51% | 50% | 42% | 34% | 22% | 18% | 1% |

(4 hour chromium release assay E:T ratio 5:1)

In Vivo Tumour Protection Assay

The ability of anti-viral CTLs to interact with cancer cells targeted with the HLA-class I peptide complexes was assayed in a tumour protection assay in SCID mice. After inoculation of the tumour cells the animals were monitored and sacrificed at day 60 when signs of disease became apparent. After sacrifice the mice were dissected and the tumour tissue weighed.

The results of the 3 groups were;

Group A (Day 1 Clone 25, Day 2 Daudi+B9E9+HLA-A2/M1)
1/Tumour mass 2.4 g
2/No tumour
3/No tumour
4/No tumour Group B (Day 1 Clone 25, Day 2 Daudi-native)
1/Tumour mass 5.64 g
2/Tumour mass 0.66 g
3/Tumour mass 1.54 g
4/Tumour mass 2.36 g Group C (Day 1 PBS, Day 2 Daudi+B9E9+HLA-A2/M1)
1/Tumour mass 3.78 g
2/Tumour mass 1.50 g
3/Tumour mass 3.06 g
4/Tumour mass 3.47 g Thus, use of the cellular immune system to selectively attack cancer cells according to the present invention has been demonstrated.

There are an increasing number of tumour associated peptides described that may serve to immunologically distinguish cancer from normal cells, and may therefore be useful in targetting aspects of the present invention. Particularly suitable are tumour specific or tumour associated cell surface antigens that can be bound by monoclonal antibodies. A number of these antibodies are now available, and could be adapted to deliver complexes of the present invention to the surface of tumour cells.

The production of large numbers of CTLs reactive with viral epitopes useful in the present invention is relatively easy in vivo as a result of infection by the relevant virus(es) and/or vaccination with said viral epitope(s). These CTLs may even be prepared/supplied ex vivo by specific antigenic stimulation.

The use of antibody targeted HLA class I/peptide complexes to redirect the lytic action of CTLs having anti-viral specificity against tumour cells according to the present invention is demonstrated. Antibody targeted HLA class I tetramers may be used, and a range of tumour cells targeted may be effectively killed by anti-viral CTLs. These aspects of the present invention are further illustrated by the in vivo data presented herein.

The applicant has advantageously reduced the number of targeting steps to 2 in this example by the use of the B9E9-sfvScSA fusion protein.

To investigate if binding of B9E9 to the Daudi cells used in the in vivo examples had any effect itself on said cells, the applicant examined the effects of binding B9E9 on cell growth. The results shown in table 1 (EX4) demonstrate that there was no significant effect on cell growth. Thus, without wishing to be bound by theory, the effects observed clearly flow from the methods of the present invention, and not from a mere effect of antibody binding.

The results shown in table 2(EX4) demonstrate that significant lysis of tumour cells occurs in vitro even at very low concentrations of the biotinylated HLA class I/M1 complex. Only at levels of 50 pg/ml or below does the degree of lysis begin to reduce slightly and activity is maintained down to 5 pg/ml. The very high affinity of biotin-streptavidin interaction ($10^{-15}$M) means that binding takes place efficiently even at these low concentrations. In a clinical scenario, with possible difficulties of targeting access, a possible degree of antigen shedding and possibly a relatively short half-life of 3 polypeptide chain types of recombinant HLA class I molecules, this advantageous feature of the present invention (ie. the ability to produce functionally effective targeting at low HLA concentrations and/or to produce effective CTL mediated lysis with only relatively small numbers of molecules immobilised on each target cell) may be very valuable.

Function of the system in vivo is demonstrated. Of the animals pre-treated with the anti-HLA-A2/M1 CTL clone 25 and then injected with targeted Daudi cells, only 1 of the 4 developed a tumour. In contrast, the control groups (ie.either mice pre-treated with clone 25 but receiving native Daudi cells, or mice with no CTL pre-treatment receiving targeted Daudi cells), all 4 of each group developed tumours.

Thus, it is demonstrated that anti-viral CTLs can effectively interact in vivo with these cells and are effectively targeted with antibody targeted HLA class I/peptide complexes according to the present invention.

The low toxicity of the targeting antibody and of the recombinant HLA class I peptide complexes demonstrates that sufficient molecules may be delivered to target cells, facilitating effective CTL activity according to the present invention.

HLA stability may advantageously be improved by the production of single chain recombinant versions.

Production of CTLs by vaccination, or the administration of CTLs expanded ex vivo such as described for the treatment of EBV associated lymphoma (Savoldo et al 2000) may be advantageously employed in the present invention.

| HLA conc | Clone 25 E:T 8:1 | Clone 25 E:T 10:1 | Clone 12 E:T 5:1 |
|---|---|---|---|
| 10 ug/ml | 91% | | |
| 5 ug/ml | 38% | | |
| 1 ug/ml | 69% | | |
| 100 ng/ml | 69% | | |
| 10 ng/ml | 46% | 97% | 42% |
| 1 ng/ml | 75% | 85% | 51% |
| 0.5 ng/ml | — | 79% | 50% |
| 0.1 ng/ml | 49% | 87% | 42% |
| 0.05 ng/ml | — | — | 34% |
| 0.01 ng/ml | 27% | 44% | 22% |
| 0.005 ng/ml | — | 26% | 18% |
| 0.001 ng/ml | 13% | 12.8% | 1.4% |

Example 5

Induction of Viral and Tumour Specific CTL Responses Using Antibody Targeted HLA Class I Peptide Complexes Introduction A central aim of cancer immunotherapy is the induction of effective cytotoxic T cell activity that recognises HLA class I/peptide complexes that are either specific to or over-represented on tumour cells (Rosenberg, 1996). There is increasing evidence that low levels of CTLs specific for 'tumour' peptides are present in a number of malignancies (Pittet et al, 1999), however the magnitude of these pre-existing responses frequently appears to be insufficient for effective in vivo activity.

The interaction between the HLA class I/peptide complex and the T cells antigen receptor is the final pathway in the expansion of CD8+ve CTLs. A range of approaches aim to reach this interaction, starting with either defined tumour associated peptide or more complex cellular based preparations. These methods include vaccination with peptides (Rosenberg et al, 1998), naked DNA (Mincheff et al, 2000) or irradiated tumour cells (Chan and Morton, 1998), these systems rely on processing and presentation by native antigen presenting cells (APCs). Alternatively ex vivo expanded dendritic cells can be used either with peptide pulsing (Hsu et al, 1996, Brossart et al, 2000), loading with tumour lysate (Nestle et al, 1999) or transfected with genes encoding tumour proteins (Wang B et al, 2000). Recombinant HLA-class I/peptide complexes either immobilised on beads (Lone et al, 1998, Tham et al, 2001), incorporated into antibody based fusion proteins (Cullen et al, 1999), or as recombinant MHC tetramers (Wang T et al, 2000) have also produced effective CTL responses both in vitro and in pre-clinical models. Dendritic cells are the most effective APCs but are present in low numbers in vivo and are difficult to culture, in contrast B cells are present in large numbers, are simple to manipulate in vitro and have been demonstrated to act effectively as APCs inducing specific CTL responses in vivo (Gajewski et al, 2001).

In a previous example we demonstrate that HLA class I/viral peptide complexes targeted to B cells via an antibody delivery system can serve as effective targets for the lytic action of anti-viral CTLs (see also Ogg et al, 2000, Savage et al, 2002). In this example we have used a similar system to investigate if the 2-step antibody delivery system (see FIG. 12) is able to produce the specific expansion of CTLs of chosen specificities from unselected populations of PBMCs.

Materials and Methods

Antibodies

The B9E9 scFvSA fusion protein contains the single-chain variable region of the murine IgG2a anti-CD20 murine antibody B9E9 fused to the genomic streptavidin of Streptomyces avidinii. The protein is secreted into the periplasm of genetically engineered *E. coli* as monomeric subunits (43,400 Daltons) that spontaneously fold into soluble tetramers with a molecular weight of 173,600 Daltons. The four antigen-binding and biotin-binding sites of the fusion protein retain the functional capabilities of the parent molecules (Schultz et al, 2000). The FITC conjugated monoclonal antibodies used in flow cytometry were anti-MHC class I (W6/32) (Cymbus Biotechnology, Harrow, UK), anti-CD19, anti-CD80 and anti-CD86 (Dako, Ely, UK).

Cells

The CIR-A2 (Storkus et al, 1989) and Daudi (Klein et al, 1968) cell lines were grown in RPMI+10% FCS supplemented with Penicillin and Streptomycin in a 37° C. incubator with 5% $CO_2$. PBMCs were isolated from healthy volunteers and melanoma patients previously documented to be HLA-A2+ve. Approximately 30 mls of venous blood was obtained by venepuncture and unfractionated PBMCs were obtained by differential centrifugation using Histopaque (Sigma, Poole, UK).

HLA-A2/Peptide Complex Monomers and Tetramers

Recombinant HLA-A2 class I molecules were obtained from ProImmune Ltd, (Oxford Science Park, Oxford UK). In brief, recombinant HLA-A2 heavy chain and beta-2 microglobulin were produced in *E. Coli*. The functional HLA class I/peptide complex were produced by refolding around the peptide of choice and then biotinylation via the Bir A site on the HLA heavy chain. (Garboczi et al, 1992, Altman et al, 1996)

The peptides used in these experiments were Influenza virus M1 peptide GILGFVFTL (SEQ ID NO: 4) (Gotch et al, 1987), Epstein-Barr virus (EBV) BMLF1 peptide GLCTLVAML (SEQ ID NO: 5) (Steven et al, 1997) and the modified melanoma associated Melan A peptide ELAGIGILTV (SEQ ID NO: 6) (Valmori et al 1998). The PE conjugated fluorescent HLA-A2/peptide tetramers of the same specificities used for flow cytometric analysis were also obtained from ProImmune.

Methods

Targeting of B9E9 scFvSA and HLA-A2/Peptide Complexes to HLA Class I –ve B Cells.

HLA class I –ve Daudi cells were used to investigate the binding of the HLA-A2/class I peptide complexes via the B9E9 scFvSA. Cells were washed in PBS and incubated with B9E9 scFvSA diluted in PBS at 10 ug/ml for 1 hour at RT. After washing the cells were incubated with either biotinylated HLA-A2/M1 peptide complexes at 0.5 ug/ml or PBS alone for 30 minutes at RT. After further washing the two groups of cells were resuspended in RPMI+10% FCS and grown at 37° C. in a 5% $CO_2$ atmosphere. At various time points parallel samples of cells were removed, washed and incubated for 30 minutes at RT with FITC conjugated W6/32, after washing the cells were analysed by flow cytometry.

The effects of B9E9 scFvSA binding on the expression of co-stimulatory molecules in PBMC B cells.

PBMCs prepared by differential centrifugation were incubated with B9E9 scFvSA (10 ug/ml), IL-7 (10 ng/ml), B9E9 scFvSA and IL-7 or PBS alone for 1 hour at RT. After washing the cells were placed into tissue culture media and returned to culture at 37° C. Samples were removed and double stained with PE conjugated anti-CD19 and either FITC conjugated anti-CD80 or anti-CD86 and analysed on a Becton Dickinson FACScan using FACScomp software.

In Vitro Immunisation Protocol

PBMCs were incubated with the B9E9 scFvSA (10 ug/ml) diluted in PBS for 1 hour at RT. After washing cells were incubated with the biotinylated HLA class I/peptide complex (0.5 ug/ml in PBS) for 30 minutes at RT. Various controls, omitting the B9E9 scFvSA or the HLA class I/peptide complex were also performed. After washing, cells were placed into 24 well plates at $3\times10^6$ cells per well and cultured in RPMI with 10% human AB serum. IL-7 (R and D Systems, Minneapolis, Minn.) was added on day 1 at 10 ng/ml and IL-2 (Chiron, Harefield, UK) was added at 10 U/ml on day 4 and every further 3 days following the method described by Lalvani (Lalvani et al, 1997). In the experiments with a second stimulation cycle further PBMCs were obtained and treated as above. These new cells were then mixed with the existing culture at a 1:2 ratio and the culture continued for a further 8 days.

Flow Cytometry and Tetramer Analysis

To stain CD8+ve cells from the PBMC culture approximately $1\times10^6$ cells were washed in PBS, resuspended and incubated with tetramer solution for 30 minutes at 37° C. followed by FITC conjugated anti-CD8 for 20 minutes at 4° C. After incubation the cells were washed, resuspended in PBS and analysed by dual colour flow cytometry. The results of flow cytometry analysis of dual stained PBMCs are shown with anti-CD8 (Y axis) and HLA-A2/M1 tetramers (X axis). Percentage figures relate to the number of tetramer positive CD8 +ve cells from the total CD8 +ve population.

Chromium Release Assay

Daudi or CIR-A2 cells were labelled with 2 uCi/uL of $^{51}Cr$ (Amersham Pharmacia, UK) for 1 hr at 37° C. then washed. Daudi cells were sequentially coated with B9E9 sfvScSA and HLA-A2/M1 complexes following the method above whilst CIR-A2 cells were pulsed with the peptide of choice at a concentration of 10 uM for 1 hr at 37° C. The target cells were plated at 3000 cells per well in U bottomed 96 well plates. PBMCs, media or 5% Triton X-100 were added to a final volume of 200 ul. Plates were incubated for 4 hours at 37° C. in a 5% $CO_2$ atmosphere and 50 ul of supernatant was collected and added to 150 ul of scintillant.

The specific lysis was calculated as:

% lysis = experimental cpm − spontaneous cpm × 100 maximum cpm − spontaneous cpm

The spontaneous release was measured from the cells incubated in media alone, the maximum release was measured from the cells incubated in 5% Triton.

Results

1 Sequential Analysis of the Binding of Biotinylated HLA-A2/M1 Complexes to Daudi B-Cell Lymphoma Cells Via B9E9 scFvSA.

Figure 13:
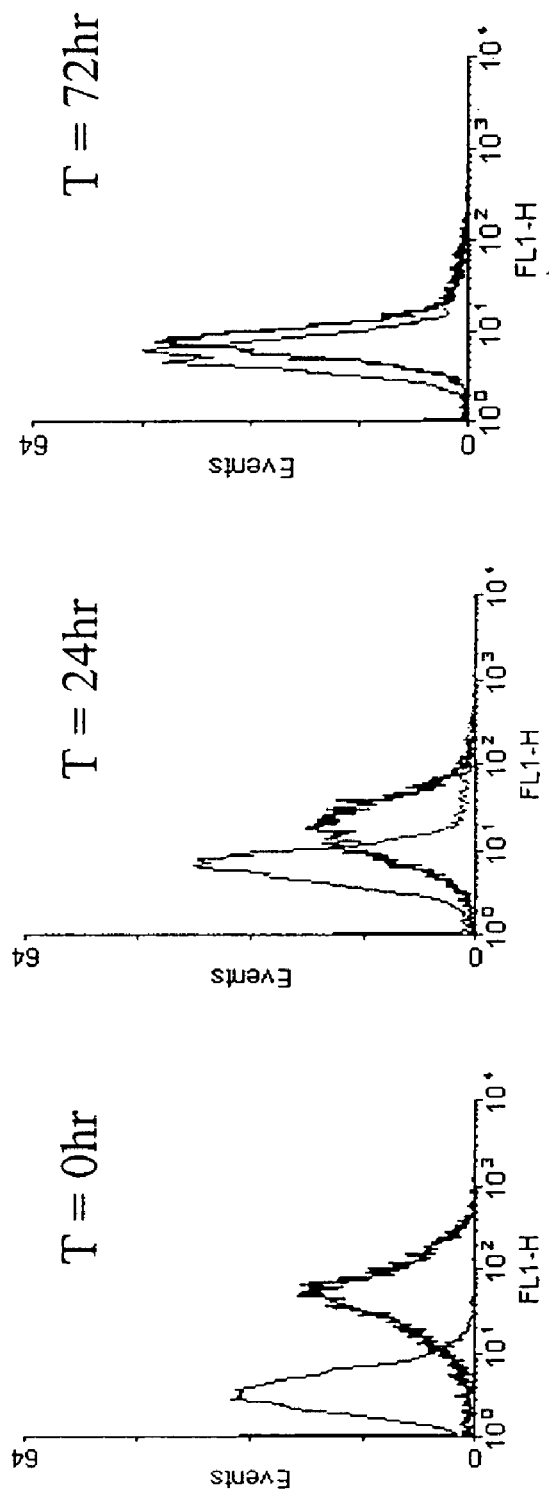
FIG. 13. Shows time course analysis of HLA-A2/M1 complexes immobilized on the surface of HLA-class 1 –ve Daudi cells via B9E9 sfvScSA. Complexes are detected via the binding of W6/32 which binds conformationally correct HLA-class I. Daudi cells targeted with B9E9 sfvScSA alone are shown in grey, in black are Daudi cells targeted with B9E9 sfvScSA and HLA-A2/M1.

The time course of the retention of the targeted HLA-A2/M1 complexes retention the HLA class I −ve Daudi cells is demonstrated in the sequential flow cytometry analyses in FIG. 13. An increased fluorescence signal is demonstrated in the targeted cells which decreases with time. However a positive signal is still maintained at +72 hours and it is probable that HLA class I/peptide complexes persist at functional levels beyond this time.

2 Effects of B9E9 scFvSA Binding on the Expression of Co-Stimulatory Molecules in PBMC B Cells.

Figure 14:
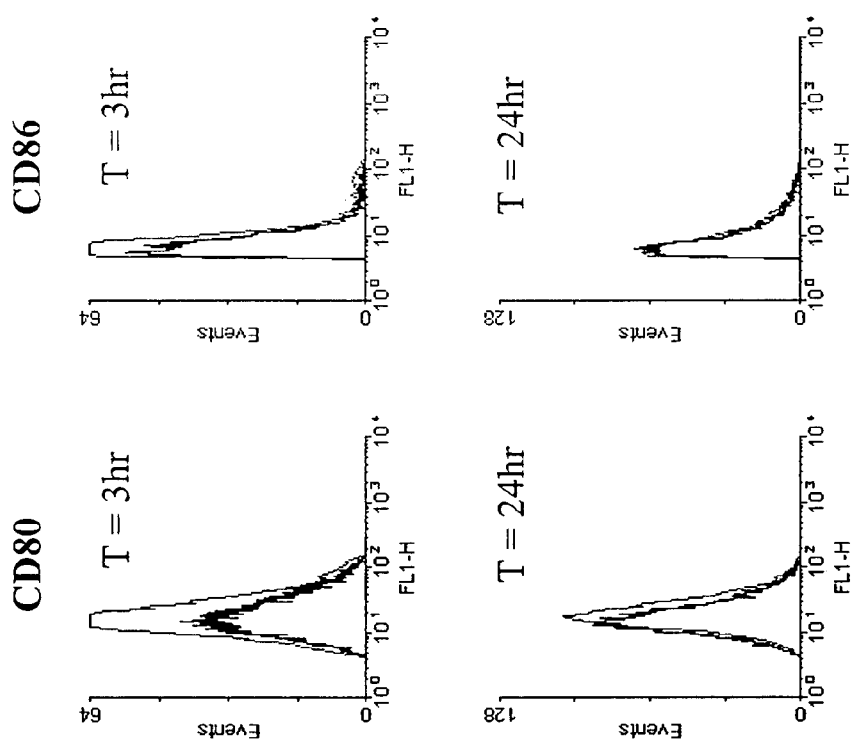
FIG. 14. Shows sequential flow cytoemetry analysis of expression of CD80 and CD86 on CD19+ve B cells within the PBMC population. The unstimulated controls are shown on the narrow trace, the experimental results from PBMCs targted with the B9E9 sfvScSA are shown in bold.

FIG. 14 demonstrates that the addition of B9E9 sfvScSA has no detectable effect on the expression of CD80 or CD86 on the B cells within the PBMC population. The results show the flow cytometry results for CD19 +ve cells at 3 hrs and 24 hrs. PBMCs treated with IL-7 alone or the combination of B9E9 sfvScSA and IL-7 also demonstrated no change in the levels of expression of CD80 and CD86. (Data not shown)

3a) Induction of CTL Activity with Targeted HLA Class I/Peptide Complexes.

Figure 15:
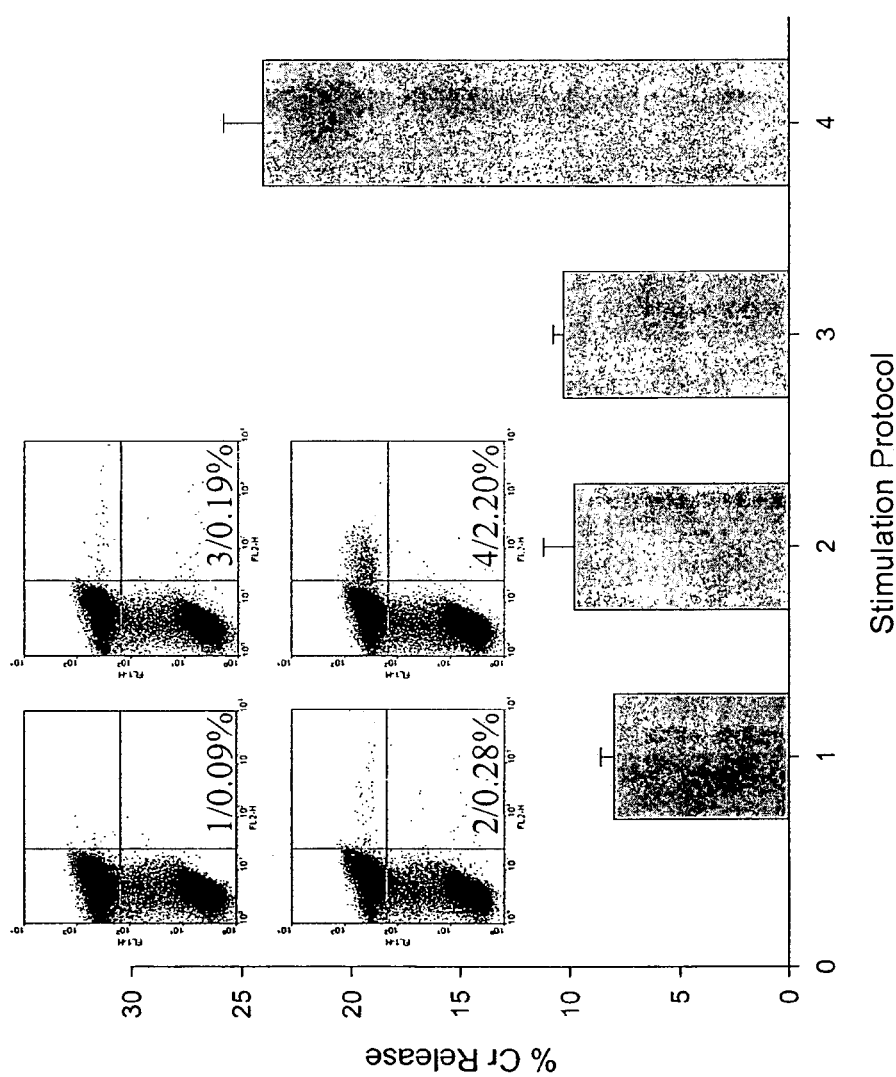
FIG. 15. Shows FACs and Cr release assay results from PBMCs stimulated with targeted HLA-A2/M1 complexes. Tetramer results demonstrate staining with anti-CD8 and HLA-A2/M1 tetramer. The Cr release assay demonstrates activity against Daudi cells bearing HLA-A2/M1 complexes. Stimulation protocols:1/PBMCs alone, 2/PBMCs+ B9E9 sfvScSA, 3/PBMCs+free HLA-A2/BMLF1, 4/PBMCs+B9E9 sfvScSA+HLA-A2/BMLF1.

The ability of the antibody targeted complexes to stimulate CTL expansion was initially examined with the HLA-A2/M1 combination. In FIG. 15 the tetramer analysis of the CD8 +ve/HLA-A2/M1 positive cells within the unstimulated PBMCs (1), PBMCs targeted with the B9E9 sfvScSA (2), and PBMCs exposed to free soluble HLA-A2/M1 complexes at 0.1 ng/ml (3) demonstrate values of 0.06% to 0.22%. In contrast the PBMCs targeted with the B9E9 sfvScSA and HLA-A2/M1 complexes (4) demonstrated 2.33% tetramer positive CD8+ve cells. Using the unfractionated PBMCs at E:T 10:1, a 4 hour Cr release assay, using HLA-A2/M1 coated Daudi cells as target cells, demonstrated a maximum of 10% lysis from the 3 control experiments but 24% from the PBMCs stimulated with HLA-A2/M1 complexes attached via the B9E9 sfvScSA fusion protein.

3b) Induced CTL Responses are Specific for the Targeted Complex.

Figure 16:
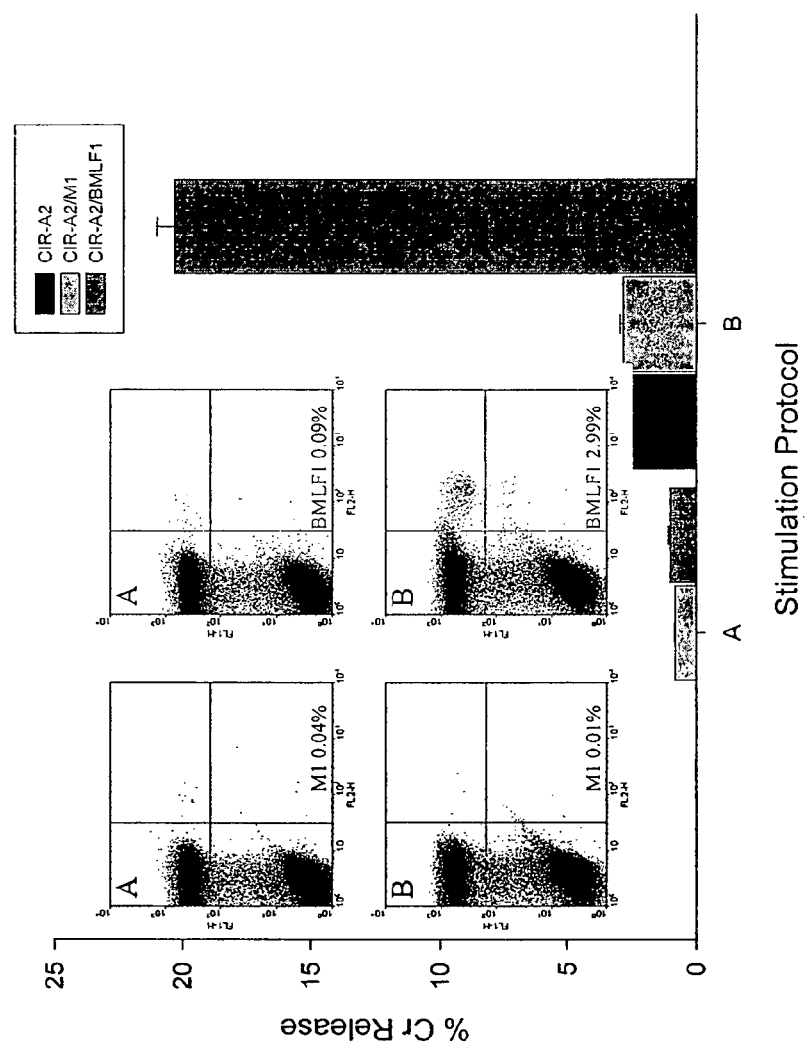
FIG. 16. Shows FACs and Cr release assay results from PBMCs stimulated with either A) B9E9 sfvScSA alone or B) B9E9 sfvScSA and targeted HLA-A2/BMLF1 complexes. Tetramer staining results are shown for both HLA-A2/M1 and HLA-A2/BMLF1. The Cr release assay demonstrates PBMC at E:T 10:1 against native/M1/BMLF1 peptide pulsed CIR-A2 target cells.

To confirm the specificity of CTL expansion, PBMCs were targeted with either B9E9 sfvScSA alone (A) or B9E9 sfvScSA and HLA-A2/BMLF1 complexes (B). In FIG. 16 the tetramer analysis of the PBMCs targeted with B9E9 sfvScSA alone demonstrates background staining of 0.04% with HLA-A2/M1 and 0.09% with HLA-A2/BMLF1. In the Cr release assay against CIR-A2 cells either native or pulsed with M1 or BMLF1 peptide the PBMCs showed no significant activity. In contrast PBMCs targeted with the HLA-A2/BMLF1 complexes demonstrate 2.99% staining with the HLA-A2/BMLF1 tetramer but with only a background staining level of 0.01% with the HLA-A2/M1 tetramer. These cells produced 20% lysis of the BMLF1 pulsed CIR-A2 target cells without any significant action on native or M1 pulsed cells.

3c) CTL Responses to a Single Cycle of Stimulation with HLA-A2/Peptide Complexes in Healthy Donors and Melanoma Patients.

The numerical values of the tetramer results from PBMCs from a series of healthy donors and melanoma patients are demonstrated in Table 1.

In response to stimulation with targeted HLA-A2/M1 complexes a greater than 5 fold increase in the number of tetramer +ve cells are seen in 6 of the 8 volunteers and one of two melanoma patients. From the HLA-A2/BMLF1 stimulated cells one of the 5 volunteers showed a greater than 5 fold increase with 2 others showing apparent increases. In response to targeted HLA-A2/Melan A complexes greater than 3 fold increases in tetramer positive cells were seen in 3 of 4 volunteers and in one of the melanoma patients.

TABLE 1 (Ex 5)

Figure 17:
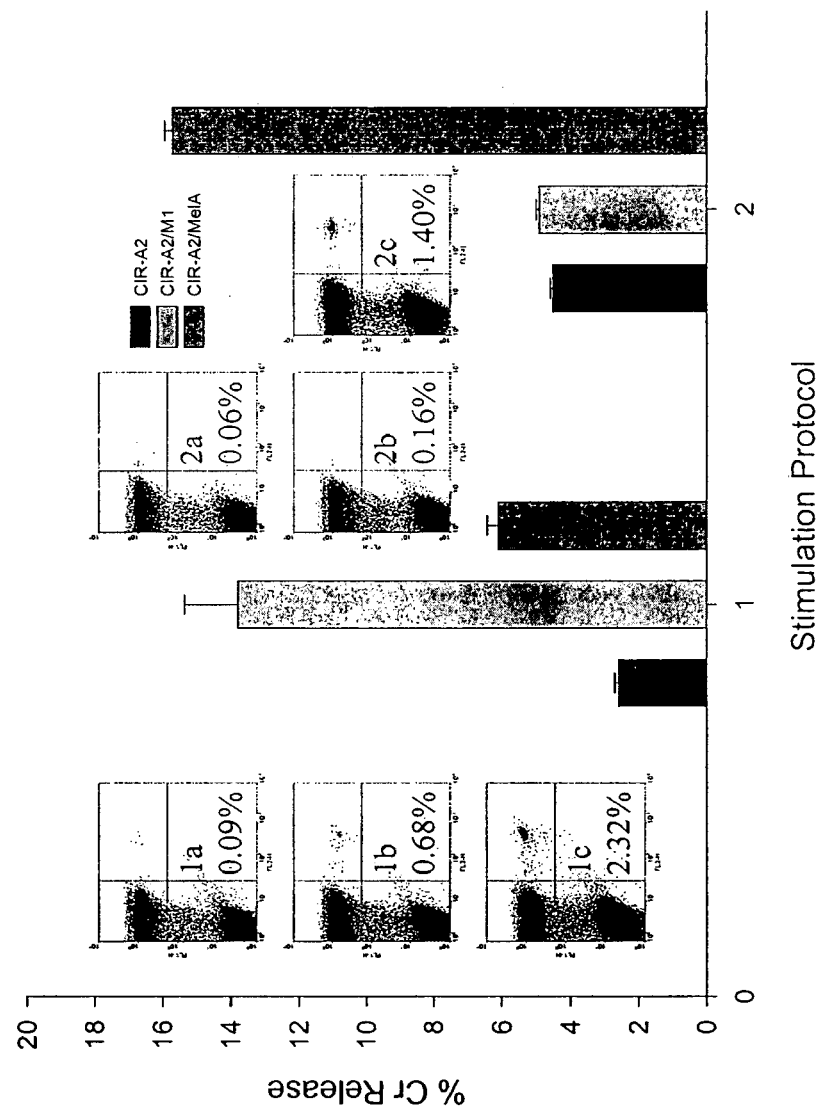
FIG. 17. Shows FACs and Cr release assay results from PBMCs stimulated twice with either 1) targeted HLA-A2/M1 complexes or 2) targeted HLA-A2/Melan A complexes. Tetramer results are a/unstimulated, b/targeted once and c/targeted twice. The Cr release assay with twice targeted PBMCs shows the activity against native and peptide pulsed CIR-A2 cells at E:T 20:1.

| | HLA-A2 + M1 ($2^{nd}$ and $3^{rd}$ columns) + BMLF1 ($4^{th}$ and $5^{th}$ columns) + MelanA ($6^{th}$ and $7^{th}$ columns) | | | | | |
|---|---|---|---|---|---|---|
| Don | 0 | 1 | 0 | 1 | 0 | 1 |
| RT | 0.21 | 1.08 | 0.54 | 0.63 | — | — |
| SL | 0.04 | 0.41 | 0.28 | 0.26 | — | — |
| JaR | 0.00 | 0.32 | 0.30 | 0.85 | — | — |
| LO | 0.00 | 0.01 | 0.08 | 0.31 | — | — |
| LL | 0.09 | 2.20 | 0.09 | 2.99 | 0.06 | 0.26 |
| CJ | 0.16 | 0.57 | — | — | 0.04 | 0.13 |
| JuR | 0.07 | 0.52 | — | — | 0.09 | 0.08 |
| DV | 0.07 | 0.80 | — | — | 0.03 | 0.14 |
| BB* | 0.00 | 0.22 | — | — | 0.41 | 1.33 |
| DB | 0.36 | 0.91 | — | — | 0.42 | 0.21 | d) CTL responses to HLA-A2/M1 and Melan A can be enhanced by a repeated stimulation FIG. 17 demonstrates the CTL responses produced by 2 rounds of in vitro stimulation using the same HLA-A2/peptide complex. The 4 hr Cr release assay (E:T 20:1) demonstrates that PBMCs stimulated with targeted HLA-A2/M1 complexes on both day 1 and day 8 produce 14% lysis of the CIR-A2 M1 pulsed cells compared with 3% lysis of native and 6% lysis of CIR-A2 melanA pulsed cells. The increase in HLA-A2/M1 specific CTLs is shown in the tetramer series with 0.09% from unstimulated cells (1A), 0.68% after one cycle (1B) and 2.32% after two cycles (1C). In this donor similar results were seen with responses to melan A with a 15% lysis of CIR-A2 cells pulsed with the Melan A peptide and increases in tetramer staining from a background of 0.06%, 0.16% after one cycle and 1.40% after two cycles. In this experiment cycles subject to one cycle of stimulation did not produce detectable activity in the Cr release assay. (Data not shown).

Discussion

The induction of an effective immune response against malignant cells has been an aim of cancer research for over a century. With the increasing understanding of how the immune system may differentiate between normal and malignant cells a number of cancer vaccine approaches have been examined. To date many of these have centred on the use of undefined antigens via tumour cell lysates or irradiated cells. However with the identification of a number of potential tumour peptide epitopes (Boon and van der Bruggen, 1996, Vonderheide et al, 1999) and the ease of manufacture of recombinant HLA class I peptide complexes (Garboczi et al, 1992) it is now feasible to consider highly specific approaches to cancer vaccine strategies.

Purified immobilised HLA class I/peptide complexes have been shown to interact and stimulate CTLs when attached to tissue culture plates (Kane et al, 1989), chemically attached to cells (Anjeure et al, 1995, Walter et al, 1997) or when coated onto beads (Motta et al, 1998). More recently antibody targeted HLA class I/peptide complexes have been demonstrated to successfully interact with CTLs to permit lysis of targeted cells in vitro (Ogg et al, 2000, Robert et al, 2000).

The ability of B cells targeted with HLA class I/peptide complexes to induce CTL responses is clearly shown in FIGS. 15, 16 and 17. In vitro CTL responses demonstrated by tetramer and Cr release assays were obtained when the HLA class I/peptide complexes were targeted to PBMCs pre-treated with the B9E9 sfvSA fusion protein. In contrast free HLA class I/peptide complexes produced no apparent responses indicating a requirement for either multimerisation or immobilisation of HLA class I/peptide complexes for effective CTL stimulation as previously described (Motta et al, 1998, Abastado et al, 1995).

The specificity of the CTL expansion is confirmed by the results shown in FIG. 16 where increases in tetramer staining and lysis of peptide pulsed target cells was only seen in response to stimulation with that specific HLA/peptide complex.

The ability of this system to further increase responses by repeated stimulation is shown in the tetramer stain results of FIG. 17. Here the frequencies of CTLs reactive with HLA-A2/M1 increase from 0.09% to 2.32% after a second cycle. In this donor the MelanA results of 0.06% and 1.4% show as similar pattern, with positive Cr release assays after 2 cycles.

The efficiency of CTL induction, has previously been shown to be related to the stability and length of expression of the HLA class-I complex on the surface of antigen presenting cells (van der Burg et al, 1996, Micheletti et al, 1999, Valmori et al, 1998). In this antibody targeting system we have aimed to optimise the time course for expression of the HLA class I complexes, by using complexes with long half lives and a high affinity binding system to a non-internalising B cell marker. The ability of these complexes to persist in a conformationally correct form for at least 72 hours on the surface of the B cells is demonstrated in FIG. 13. It is probable that functionally active levels of complexes remain on the surface of the B cells for a longer period, we have previously shown that CTLs interact efficiently with B cells with levels of targeted HLA below that detectable by cytometry (Savage et al, 2002).

The data in FIG. 14 demonstrates that binding of the B9E9 sfvScSA to the B cells within the PBMCs either alone or in conjunction with IL-7 had no effect on the expression of B80 and B86. Whilst the enhanced expression of co-stimulatory molecules generally increases CTL responses, it has previously been demonstrated that effective CTL can be produced without accessory molecule expression, particularly when high epitope densities are used (Wang et al, 2000).

At present there has been only limited optimisation of this in vitro stimulation protocol with significant differences in the levels of CTL responses between individuals. However in all experimental cultures using targeted HLA class I/peptide complexes significant inhibition of proliferation compared to those targeted with the B9E9 fusion protein alone was observed (data not shown). It is possible that the effect of the supra-physiological stimulation prevents expansion of the specific CTL population either via a direct apoptotic action or the result high levels of cytokine production within the closed system. Studies in mice have shown that increased antigenic density can result in higher CTL activity but produces a significant reduction at very high densities (Wherry et al, 1999). Similarly in human systems the presence of supra-optimal levels of HLA class I complexes can lead to apoptosis rather than expansion of stimulated CD8+ve CTLs (Alexander-Miller et al, 1998). As CD20 is present at approximately 50,000 copies per B cell (Marti et al, 1992), saturated binding of HLA class I/peptide complexes could result in 50,000-200,000 copies of a single peptide/HLA class I combination per cell. This is significantly higher than produced by peptide pulsing which results in peptide placement in 5,000 copies of an individual HLA allele (Delon et al, 1998) out of a total allele number of $10^5$ per B cell. (Kageyama et al, 1995, McCune et al, 1975) Additionally the stability of the recombinant complexes appears to be greater than those produced by peptide pulsing which have an average ½ life of only 2.5-4 hrs (Wataya et al, 2001) which may further increase the strength and duration of T cell activation.

The ability of this system to specifically induce the expansion of CTLs to a specific peptide/HLA-class I complex will prove useful for in vitro studies analysing the endogenous CTL response or the effects of other in vivo procedures. Potentially this system could also be used for the ex vivo production of CTLs for the adoptive immunotherapy of cancer and other diseases. However a vaccination procedure based on targeting HLA class I/peptide complexes to APCs in vivo via an antibody delivery system could offer significant advances in both the applicability and effectiveness of cancer vaccines.

The B9E9 sfvSA fusion protein is currently in clinical trials for the treatment of B cell lymphoma using radiolabelled biotin as the effector function. The ease of administration, lack of toxicity and option for repeated doses suggest that using this molecule in a vaccine strategy should be feasible. To date recombinant HLA class I molecules are yet to be administered to cancer patients, however as endogenous HLA class I molecules circulate in health and in increased levels in a number of illnesses (McMillan et al, 1997) they are unlikely to have any direct toxicity.

In this work we have focused on stimulation with a single HLA class I/peptide complex, however the ability to make these recombinant molecules of any chosen HLA class I/peptide combination should allow for vaccination with a range of complexes either sequentially or concurrently. As the stability of the HLA class I/peptide complexes appears to varying considerably with the identity of the peptide (Valmori et al, 1998) and stability is closely linked to the immunogenicity of a chosen HLA class I/peptide complex, it is possible that recombinant molecules that incorporate the peptide/HLA heavy chain/beta-2-microglobulin into fusion proteins may offer potential benefits.

Currently optimisation of the level of targeted HLA class I/complexes on the targeted B cells and the cytokine support for the most effective stimulation and induction of CTL responses in vitro is being examined. Potential clinical studies will initially use PBMCs targeted with complexes ex vivo, which will allow accurate administration of designated numbers of targeted cells at the opyimum epitope density. Considering the potential clinical applicability of this system, it is probable that initially PBMCs will be targeted with complexes ex vivo, potentially via a closed leucapheresis system. This approach should also minimise the potential immunogenicity of the streptavidin in the fusion protein and the potential risk of uncontrolled CTL expansion that could occur with intravenous HLA classI/complex administration that would result in the targeting of the total B cell population.

Summary

The production of cytotoxic T cells (CTLs) with specificity for cancer cells is a rapidly evolving branch of cancer therapeutics. A variety of approaches aim to amplify anti-tumour CTL responses using purified peptides, tumour cell lysates or recombinant HLA/peptide complexes in differing antigen presenting systems.

Using a two-step biotin-streptavidin antibody targeting system, recombinant HLA-class I/peptide complexes were attached to the surface of B cells via the anti-CD20 B9E9-scFvSA antibody-streptavidin fusion protein. Flow cytometry with a conformation dependant monoclonal antibody to HLA class I indicated that targeted HLA-class I/peptide complexes remain on the surface of B cells in culture for periods in excess of 72 hours. PBMCs were stimulated in vitro for 8-14 days using the autologous B cells as antigen presenting cells. Following a single cycle of stimulation specific CTL responses to targeted HLA-A2 complexes containing the M1, BMLF1 and Melan A peptides could be demonstrated by tetramer staining and Cr release assays. With the HLA-A2/BMLF1 complex up to 2.99% of CD8+ve cells were tetramer positive producing 20% lysis (E:T 10:1) of CIR-A2 target cells in an in vitro cytotoxicity assay compared to baseline levels of 0.09% tetramer +ve and 2% lysis in the unstimulated population. PBMCs from a healthy donor treated with two cycles of stimulations with targeted HLA-A2/Melan A complexes, demonstrated expansion of the melanA tetramer +ve population from 0.03% to 1.4% producing 15% lysis of Melan A pulsed target cells.

With further consideration to the key variables of HLA/peptide complex density, the ratio of stimulator to effector cells and optimum cytokine support, this system should offer an easy and effective method for the in vitro amplification of specific CTL responses and warrants development for the in vivo induction of CTL responses in cancer therapy.

Example 6

Treatment of a Blood Sample

Protocol for the ex vivo preparation and re-administration of autologous B cells treated with antibody targeted HLA class I/peptide complexes.
1/Take 600 ml of venous blood into standard transfusion bag
2/Transfer to blood transfusion laboratory for work in sterile GLP conditions
3/Centrifuge to prepare 'buffy' coat from 600 mls of whole blood
4/Wash in sterile PBS×1
5/Resuspend in 50 mls sterile PBS
6/Incubate with B9E9 sfvscSA at 10 ug/ml for 30 minutes at room temperature
7/Wash in sterile PBS×3
8/Resuspend in 50 mls sterile PBS.
9/Incubate with biotinylated HLA class I/peptide complex (es) at 0.5 ug/ml for 10 minutes at room temperature.
10/Wash in sterile PBS×1
11/Resuspend in 50 mls of sterile PBS
12/Re-infuse into patient via peripheral venous access over 10 minutes.

The invention will now be further described by the following numbered paragraphs:

1. A complex comprising an HLA class I molecule or fragment thereof, which HLA class I molecule or fragment thereof comprises a T cell binding portion, arid attaching means for selectively attaching said HLA class I molecule or fragment thereof to a target cell.
2. A complex as in paragraph 1, wherein said attaching means comprises a linking polypeptide with high specific affinity for a target cell specific molecule on the surface of the target cell.
3. A complex as in paragraph 2, wherein said linking polypeptide comprises ail antibody, preferably a monoclonal antibody, raised against said target cell specific molecule.
4. A complex as in paragraph 2, wherein said linking polypeptide is adapted to be attached directly to said HLA class I molecule or fragment thereof.
5. A complex as in paragraph 2, wherein said attaching means further comprises a coupling system for coupling said linking polypeptide to said HLA class I molecule or fragment thereof.
6. A complex as in paragraph 5, wherein said coupling system comprises a two- or three-step chain of well-characterised paired small molecules, which chain is joined to the linking polypeptide and the HLA class I molecule so as to form a stable bridge between the two.
7. A complex as in paragraph 6, characterised in that said chain comprises biotin and avidin/streptavidin.
8. A complex as in paragraph 6, characterised in that said chain comprises calmodulin and calmodulin binding peptide.
9. A complex as in any preceding paragraph, which complex comprises a recombinant protein, which recombinant protein includes a moiety comprising said HLA class I molecule or fragment thereof, and a moiety comprising said attaching means.
10. A complex as in paragraph 1, characterised in that said HLA class I molecule or fragment thereof binds or is attached to a recognition peptide, which recognition peptide is arranged to be presented by said HLA class I molecule or fragment thereof for T cell recognition.
11. A complex as in paragraph 1, characterised in that said target cell is a type of cell the presence of which is undesirable in a patient, such as a tumour cell or a diseased, foreign or malignant cell such as a cancer cell, a leukaemia cell, a cell infected with the HIV virus or with any other parasite, bacterium, microbe or virus, or a cell responsible for detrimental activity in auto-immune disease.
12. A complex as in paragraph 11 appended to claim 10, wherein there is a recognition peptide that comprises a peptide which has a strong cytotoxic T cell response or which is capable of inducing a powerful immune response.
13. A complex as in paragraph 11 wherein there is a recognition peptide comprises a viral or microbial peptide, such as an influenza virus peptide, a measles virus peptide, an Epstein-Barr virus peptide, in particular an Epstein-Barr virus peptide comprising the RAKFFQLL epitope (SEQ ID NO: 1) of the lytic protein BZLF1, a Cytomegalovirus peptide, or a tetanus toxoid peptide.

14. A complex as in paragarph 11, wherein the allotype of said HLA class I molecule or fragment thereof is different front tile ailotype of tile HLA class I molecules of the patient, so that all alloreactive response call additionally or alternatively be triggered against said target cell.

15. A complex as in paragraph 1, wherein said target cell is an antigen presenting cell.

16. A complex as in paragraph 15, wherein there is recognition peptide that comprises a tumour specific peptide, or a viral peptide, or a bacterial peptide, or a parasitic peptide, or any peptide which is exclusively or characteristically presented by HLA class I molecules on the surface of diseased or malignant cells, or virally, bacterially, parasitically or microbially infected cells, or foreign cells the presence of which is undesirable in a patient.

17. A complex as in paragraph 1, wherein said target cell is a culture cell.

18. A complex as in paragraph 1, wherein said target cell is a cell in the body of a patient.

19. A method for attaching the complex of paragraph 1 to said target cell, comprising the step of introducing to said target cell said I-ILA class I molecule or fragment thereof and said attaching means.

20. Use of the complex of paragraph 15 in the in vivo or ex vivo amplification of cytotoxic T cells with specificity for said recognition peptide.

21. A method for producing or enhancing an immunological response against a target cell, comprising the step of attaching the complex of claim 1 to said target cell by introducing to said target cell a HLA class 1 molecule or fragment thereof and attaching means.

22. A method for immunising a patient against a disease or condition which is characterised by the presence in the patient's body of cells displaying said recognition peptide on the surface thereof, such as a tumour, or a malignant or auto-immune disease such as cancer or leukaemia, an infectious disease such as a viral infection such as HIV infection, a bacterial or microbial infection such as tuberculosis, or a parasitic infection such as malaria; comprising the step of administering to said patient an effective amount of the complex of paragraph 15.

23. A pharmaceutical composition for use in immunising a patient against a disease or condition which is characterised by the presence in the body of the patient of diseased, malignant or foreign cells; such as a tumour, or a malignant or auto-immune disease such as cancer or leukaemia, or an infectious disease such as a viral infection such as HIV infection, or a bacterial or microbial infection such as tuberculosis, or a parasitic infection such as malaria; said pharmaceutical composition comprising a complex as in paragraph 15 and an appropriate excipient or carrier.

24. Use of the complex of paragraph 15 in the preparation of a medicament for use in immunising a patient against a disease or condition which is characterised by the presence in the patient's body of cells displaying said recognition peptide on the surface thereof such as a tumour, or a malignant or auto-immune disease such as cancer or leukaemia, an infectious disease such as a viral infection such as HIV infection, a bacterial or microbial infection such as tuberculosis, or a parasitic infection such as malaria.

25. A method for the treatment of a disease or condition such as a tumour, or a malignant or auto-immune disease such as cancer or leukaemia, an infectious disease such as a viral infection such as HIV infection, a bacterial or microbial infection such as tuberculosis, or a parasitic infection such as malaria, comprising the step of administering to a patient in need thereof an effective amount of the complex of paragraph 11.

26. A pharmaceutical composition for use in the treatment of a disease or condition characterised by the presence in a patient of diseased, foreign or malignant cells; such as a tumour, or a malignant or auto-immune disease such as cancer or leukaemia, or an infectious disease such as a viral infection such as HIV infection, or a bacterial or microbial infection such as tuberculosis, or a parasitic infection such as malaria; said pharmaceutical composition comprising a complex as in paragraph 11 and an appropriate excipient or carrier.

27. Use of the complex of paragraph 11 in the preparation of a medicament for the treatment of a tumour, or a malignant or auto-immune disease such as cancer or leukaemia, or an infectious disease such as a viral infection such as HIV infection, or a bacterial or microbial infection such as tuberculosis, or a parasitic infection such as malaria.

28. A pharmaceutical pack or kit comprising one or more containers containing one or more of the pharmaceutical compositions in paragraph 23 and written instructions for the administration of said composition or compositions to a patient.

29. A method comprising contacting a blood sample with a complex according to paragraph 1.

30. A method comprising contacting an isolated blood sample with a complex according to paragraph 1.

31. A complex comprising an HLA class I molecule or fragment thereof, the HLA class I molecule or fragment thereof comprising:
    (i) a T cell binding portion; and
    (ii) attachment means for selectively attaching the HLA class I molecule or fragment thereof to a target cell;
    wherein the HLA class I molecule or fragment thereof binds or is attached to a recognition peptide,
    wherein the recognition peptide is arranged to be presented by said HLA class I molecule or fragment thereof for T cell recognition,
    wherein the attachment means comprises:
    (a) a linking polypeptide with specific affinity for a molecule on the surface of the target cell
    (b) a coupling system for coupling the linking polypeptide to the HLA class I molecule or fragment thereof.

32. A complex according to paragraph 31 wherein the coupling system comprises:
    a first small molecule joined to the linking polypeptide; and
    a second small molecule joined to the HLA class I molecule,
    wherein interaction of the small molecules forms a stable bridge between the linking polypeptide and the HLA class I molecule.

33. A complex according to paragraph 32 wherein the coupling system comprises a three-step chain of small molecules.

34. A complex according to paragraph 32 wherein the coupling system comprises biotin and avidin/streptavidin.

35. A complex according to paragraph 32, wherein the coupling system comprises calmodulin and calmodulin binding peptide.

36. A complex according to paragraph 31 wherein said recognition peptide comprises a peptide which elicits a strong cytotoxic T cell response or which is capable of inducing a powerful immune response.

37. A complex according to paragraph 31 wherein said recognition peptide comprises one or more of a tumour specific peptide, a viral peptide, a bacterial peptide, or a parasitic peptide.

38. A complex according to paragraph 31 wherein said recognition peptide comprises a peptide selected from the group consisting of an influenza virus peptide, a measles virus peptide, an Epstein-Barr virus peptide, an Epstein-Barr virus peptide, a peptide comprising the RAKFFQLL epitope (SEQ ID NO: 1) of the lytic protein BZLF1, a Cytomegalovirus peptide and a tetanus toxoid peptide.

39. A complex according to paragraph 31 wherein said linking polypeptide comprises an antibody or a fragment thereof.

40. A complex according to paragraph 39 wherein said antibody is a monoclonal antibody.

41. A complex according to paragraph 31 wherein the attaching means specifically binds to a molecule on the surface of an antigen presenting cell.

42. A complex comprising
   (i) a HLA class I molecule or a fragment thereof;
   (ii) an attachment means comprising either
   a) a molecule which specifically binds a polypeptide selected from the group consisting of carcinoembryonic antigen, placental alkaline phosphatase, polymorphic epithelial mucin, human chorionic gonadotrophin, CD20, prostate specific antigen, Ca-125 and HMW-MAA; or
   b) an antibody selected from the group consisting of C46, 85A12, H17E2, HMFG1, W14, 1F5, 225.28s;
   (iii) a recognition peptide selected from the group consisting of an influenza virus peptide, a measles virus peptide, an Epstein-Barr virus peptide, an Epstein-Barr virus peptide, a peptide comprising the RAKFFQLL epitope (SEQ ID NO: 1) of the lytic protein BZLF1, a Cytomegalovirus peptide and a tetanus toxoid peptide;
   wherein the recognition peptide is arranged to be presented by the HLA class I molecule or fragment thereof for T cell recognition.

43. A complex according to paragraph 42 further comprising a coupling system for joining the attachment means to the HLA molecule or fragment thereof.

44. A complex according to paragraph 43 wherein the coupling system comprises one or more of biotin, avidin, streptavidin, calmodulin or calmodulin binding protein.

45. A complex comprising
   (i) a HLA-A2 molecule or a fragment thereof, conjugated to biotin
   (ii) a monoclonal antibody 225.28s conjugated to biotin
   (iii) avidin
   (iv) a peptide comprising the amino acid sequence SLYNTVATL (SEQ ID NO: 2).

46. A method for attaching a complex according to paragraph 31 or paragraph 42 or paragraph 45 to a target cell, comprising the step of contacting the target cell with the HLA class I molecule or fragment thereof and the attaching means.

47. A method for producing or enhancing an immunological response against a target cell, comprising the step of attaching a complex according to paragraph 31 to the target cell.

48. A pharmaceutical composition comprising
   (i) a complex according to paragraph 31, and
   (ii) a pharmaceutically acceptable excipient or carrier.

49. Use of a complex according to paragraph 31 in the preparation of a medicament for induction of a cytotoxic T cell response against a cell recognised by the attachment means.

50. Use of a complex according to paragraph 1 in the preparation of a medicament for immunising a subject against said recognition peptide.

51. A kit comprising one or more pharmaceutical compositions according to paragraph 48 and written instructions for the administration of said composition(s) to a subject.

52. A method for directing a cytotoxic T cell response against a target cell, the method substantially as described herein with reference to FIG. 1.

Figure 4:
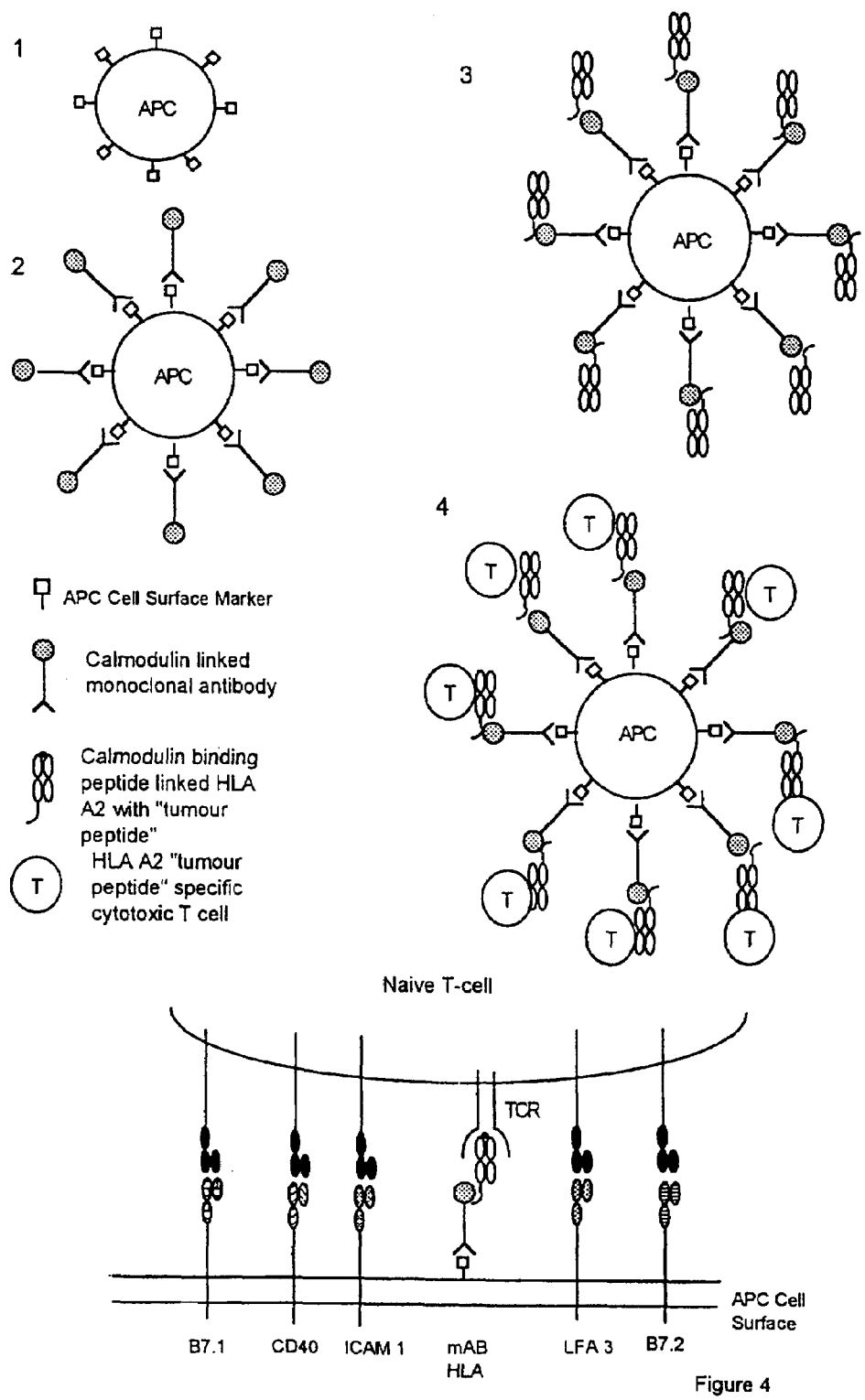
FIG. 4 shows a diagram showing the method/idea for delivering HLA class I/peptide complexes to antigen presenting cells.

53. A method for producing an immune response against a peptide, the method substantially as described herein with reference to FIG. 4.

References

Cormier, J. N., Panelli, M. C., Hackett, J. A., Bettinotti, M. P., Mixon, A., Wunderlich, J., Parker, L. L., Restifo, N. P., Ferrone, S. and Marincola, F. M. (1999) Natural variation of the expression of HLA and endogenous antigen modulates CTL recognition in an in vitro melanoma model. Int J Cancer 80, 781-790.

Zavazava, N. and Kronke, M. (1996) Soluble HLA class I molecules induce apoptosis in alloreactive cytotoxic T lymphocytes. Nature Medicine 2, 1005-1010.

Buchsbaum, R. J., Fabry, J. A. and Lieberman, J. (1996) EBV-specific cytotoxic T lymphocytes protect against human EBV-associated lymphoma in scid mice. Immunology Letters 52, 145-152.

Robert, B., Guillaume, P., Luescher, I., Romero, P. and Mach J-P. (2000) Antibody-conjugated MHC class I tetramers can target tumor cells for specific lysis by T lymphocytes. Eur. J Immunol 30, 3165-3170.

De Kroon, J. F. E. M., van Bergen, C. A. M., de Paus, R. A., Kluin-Nelemans, H. C. K., Willemze, R. and Falkenberg, J. H . F. (11997) Human cytotoxic CD8+T-lymphocyte clones engraft in severe combined immunodeficient (SCID) mice but show diminished function. Journal of Immunotherapy, 20, 101-110.

Ghetie, M. A., Podar, E. M ., Gordon, B. E., Pantazis, P., Uhr, J. W. and Vitetta, E. S. (1996) Combinationimmunotoxin treatment and chemotherapy in SCID mice with advanced, disseminated Daudi lymphoma. Int J Cancer 68, 93-96.

Gidlof, C., Dohlsten, M., Lando, P., Kalland, T., Sundstrom, C. and Totterman, T. H. (1997) A supernatgen-antibody fusion protein for T cell immunotherapy of human B lineage malignancies. Blood 89, 2089-97.

Van Ojik, H. H. and Valerius, T (2001) Preclinical and clinical data with bispecific antibodies recruiting myeloid effector cells for tumor therapy. Crit Rev Oncol Hematol 38, 47-61.

Nielsen, S. E., Zeuthen, J., Lund, B., Persson, B., Alenfall, J. and Hansen, H. H. (2000) Phase I study of single escalating doses of a superantigen-antibody fusion protein (PNU-214565) in patients with advanced colorectal or pancreatic carcinoma. J Immunother 23, 146-53.

Penichet, M. L. and Morrison, S. L. (2001) Antibody-cytokine fusion proteins for the therapy of cancer. J Immunol Methods 248, 91-101.

Hainsworth, J. D. (2000) Rituximab as first line systemic therapy for patients with low-grade lymphoma. Semin Oncol 27, 25-9.

Savoldo, B., Heslop, H. E and Rooney, C. M. (2000) The use of cytotoxic T cells for the prevention and treatment of Epstein-Barr virus induced lymphoma in transplant recipients. Leuk Lymphoma 39, 455-464.

Abastado J, Lone Y, Casrouge A, Boulot G and Kourilsky P (1995) Dimerization of soluble major histocompatability complex-peptide complexes is sufficient for activation of t cell hybridoma and induction of unresponsiveness. J Exp Med 182: 439-447

Alexander-Miller M A, Derby M A, Sarin A, Henkart P A and Berzofsky J A (1998) Supraoptimal peptide-major histocompatability complex causes a decrease in Bcl-2 levels and allows tumour necrosis factor alpha receptor II-mediated apoptosis of cytotoxic T lymphocytes. J Exp Med 188: 1391-1399

Altman J D, Moss P A, Goulder P J, Barouch D H, McHeyzer-Williams M G, Bell J I, McMichael A J and Davis M M (1996) Phenotypic analysis of antigen-specific T lymphocytes. Science 274:94-96

Anjuere F, Horvath C, Cerottini J C, and Luescher I F (1995) Induction of CTL in vivo by major histocompatibility complex class I-peptide complexes covalently associated on the cell surface. Eur J Immunol 25: 1535-1540

Boon T and van der Bruggen P (1996) Human tumor antigens recognized by T lymphocytes. J Exp Med 183: 725-729

Brossart P, Wirths S, Stuhler G, Reichardt V L, Kanz L and Brugger W (2000) Induction of cytotoxic T-lymphocyte responses in vivo after vaccinations with peptide-pulsed dendritic cells. Blood 96: 3102-3108

Chan A D and Morton D L (1998) Active immunotherapy with allogeneic tumor cell vaccines: present status. Semin Oncol 25: 611-622

Cullen C M, Jameson S C, DeLay M, Cottrell C, Becken E T, Choi E and Hirsch R (1999) A divalent major histocompatibility complex/IgG1 fusion protein induces antigen-specific T cell activation in vitro and in vivo. Cell Immunol 192: 54-62

Delon J, Bercovici N, Raposo G, Liblau R, and Trautmann A (1998) Antigen-dependent and -independent Ca2+ responses triggered in T cells by dendritic cells compared with B cells. J Exp Med 188:1473-1484

Gajewski T F, Fallarino F, Ashikari A, and Sherman M (2001) Immunization of HLA-A2+ melanoma patients with MAGE-3 or MelanA peptide-pulsed autologous peripheral blood mononuclear cells plus recombinant human interleukin 12. Clin Can Res 7: 895s-901 s.

Garboczi D N, Hung D T, and Wiley D C (1992) HLA-A2-peptide complexes: refolding and crystallization of molecules expressed in Escherichia coli and complexed with single antigenic peptides. Proc Natl Acad Sci 89: 3429-3433

Gotch F, Rothbard J, Howland K, Townsend A, McMichael A (1987) Cytotoxic T lymphocytes recognize a fragment of influenza virus matrix protein in association with HLA-A2. Nature 326: 881-882

Hsu F J, Benike C, Fagnoni F, Liles T M, Czerwinski D, Taidi B, Engleman E G and Levy R (1996) Vaccination of patients with B-cell lymphoma using autologous antigen-pulsed dendritic cells. Nat Med 2: 52-58

Kageyama S, Tsomides T J, Sykulev Y and Eisen H N (1995) Variations in the number of peptide-MHC class I complexes required to activate cytotoxic T cell responses. J Immunol 154: 567-576

Kane K P, Vitiello A, Sherman L A and Mescher M F (1989) Cytolytic T-lymphocyte response to isolated class I H-2 proteins and influenza peptides. Nature 340: 157-159

Klein E, Klein G, Nadkarni J S, Nadkarni J J, Wigzell H, Clifford P. (1968) Surface IgM-kappa specificity on a Burkitt lymphoma cell in vivo and in derived culture lines. Cancer Res 28: 1300-1310

Lalvani A, Dong L, Ogg G, Pathan A A, Newell H, Hill A V S, McMichael A J and Rowland-Jones S (1997) Optimisation of a peptide-based protocol employing IL-7 for in vitro restimulation of human cytotoxic T lymphocyte precursors. J Imm Methods 210: 65-77

Lone Y C, Motta I, Mottez E, Guilloux Y, Lim, A, Demay F, Levraud J P, Kourilsky P and Abastado J P (1998) In vitro induction of specific cytotoxic T lymphocytes using recombinant single-chain MHC classI/peptide complexes. J Immunother 21: 283-294

Marti G E, Faguet G, Bertin P, Agee J, Washington G, Ruiz S, Carter P, Zenger V, Vogt R and Noguchi P (1992) CD20 and Cd5 expression in B-chronic lymphocytic leukaemia. Ann N Y Acad Sci 651: 480-483.

McMillan R W, Gelder F B, Zibari G B, Aultman D F, Adamashvili I and McDonald J C (1997) Soluble fraction of class I human histocompatibility leukocyte antigens in the serum of liver transplant recipients. Clin Transplant 11: 98-103

Micheletti F, Bazzaro M, Canella A, Marastoni M, Traniello S and Gavioli R (1999) The lifespan of major histocompatibility complex calssI/peptide complexes determines the efficiency of cytotoxic T lymphocyte responses. Immunology 96: 411-415

Mincheff M, Tchakarov S, Zoubak S, Loukinov D, Botev C, Altankova I, Georgiev G, Petrov S and Meryman HT (2000) Naked DNA and adenoviral immunizations for immunotherapy of prostate cancer: a phase I/II clinical trial. Eur Urol 38: 208-217

McCune J M, Humphreys R E, Yocum R R and Strominger J L (1975) Enhanced representation of HLA antigens on human lymphocytes after mitogenesis induced by phytohemagglutinin or Epstein Barr virus. Proc Natl Acad Sci 72: 3206-3209

Motta I, Lone Y C and Kourilsky P (1998) In vitro induction of naive cytotoxic T lymphocyte with complexes of peptide and recombinant MHC class I molecules coated onto beads: role of TCR/ligand density. Eur J Immunol 28: 3685-3695

Nestle F O, Alijagic S, Gilliet M, Sun Y, Grabbe S, Dummer R, Burg G and Schadendorf D (1998) Vaccination of melanoma patients with peptide- or tumor lysate-pulsed dendritic cells. Nat Med 4: 328-332

Ogg G S, Dunbar P R, Cerundolo V, McMichael A J, Lemoine N R and Savage P (2000) Sensitization of tumour cells to lysis by virus-specific CTL using antibody-targeted MHC class I/peptide complexes. Br J Cancer 82: 1058-1062

Pittet M, Valmori D, Dunbar P R, Speiser D E, Lienard D, Lejeune F, Fleischhauer K, Cerundolo V, Cerottini J-C and Romero P (1999) High frequencies of naïve Melan-A/Mart-1 specific CD8+ T cells in a large proportion of human histocompatibility leukocyte antigen (HLA)-A2 individuals. J Exp Med 190: 705-716

Robert B, Guillaume P, Luescher I, Romero P and Mach J-P (2000) Antibody-conjugated MHC class I tetramers can target tumor cells for specific lysis by T lymphocytes. Eur. J Immunol 30: 3165-3170

Rosenberg S A (1996) Development of cancer immunotherapies based on identification of the genes encoding cancer regression antigens. *J Natl Cancer Inst* 88: 1635-1644

Rosenberg S A, Yang J C, Schwartzentruber D J, Hwu P, Marincola F M, Topalian S L, Restifo N P, Dudley M E, Schwarz S L, Spiess P J, Wunderlich J R, Parkhurst M R, Kawakami Y, Seipp C A, Einhom J H and White D E (1998) Immunologic and therapeutic evaluation of a synthetic peptide vaccine for the treatment of patients with metastatic melanoma. *Nat Med* 4: 321-327

Savage P, Cowburn P, Clayton A, Man S, Lawson T, Ogg G, Lemoine N, Schultz J, Epenetos A and McMichael A J (2002) Anti-viral Cytotoxic T cells inhibit the growth of cancer cells bearing antibody targeted MHC class I/peptide complexes in SCID mice. *Int J Cancer* In press.

Schultz J, Lin Y, Sanderson J, Zuo Y, Stone D, Mallett R, Wilbert S and Axworthy D (2000) A tetravalent-single-chain-antibody-streptavidin fusion protein for pretargeted lymphoma therapy. *Cancer Res* 60: 6663-6669.

Steven N M, Annels N E, Kumar A, Leese A M, Kurilla M G and Rickinson A B (1997) Immediate early and early lytic cycle proteins are frequent targets of the Epstein-Barr virus induced cytotoxic T cell responses. *J Exp Med* 185: 1605-1617

Storkus W J, Alexander J, Payne J A, Cresswell P and Dawson J R (1989) The alpha 1/alpha 2 domains of class I HLA molecules confer resistance to natural killing. *J Immunol* 143: 3853-3857

Tham E L, Jensen P L and Mescher M F (2001) Activation of antigen-specific T cells by artificial cell constructs having immobilized multimeric peptide-class I complexes and recombinant B7-Fc proteins. *J Immunol Methods* 249: 111-119

Valmori D, Fonteneau J-F, Lizana C M, Gervois N, Lienard D, Rimoldi D, Jongeneel V, Jotereau F, Cerottini J-C and Romero P (1998). Enhanced generation of specific tumour reactive CTL in vitro by selected Melan-A/MART-1 immunodominant peptide analogues. *J Immunol* 160: 1750-1758

Van der Burg S H, Visseren M J W, Brandt R M P, Kast W M and Melief C J M (1996) Immunogenecity of peptides bound to MHC class I molecules depends on the MHC-peptide complex stability. *J Immunol* 156: 3308-3314

Vonderheide R H, Hahn W C, Schultze J L and Nadler L M (1999) The telomerase catalytic subunit is a widely expressed tumor-associated antigen recognised by cytotoxic T lymphocytes. *Immunity* 10: 673-679

Walter J B, Brander C, Mammen M, Garboczi D N, Kalams S A, Whitesides G, Walker B D and Eisen H N (1997) Stimulation of human cytotoxic T cells with HIV-1-derived peptides presented by recombinant HLA-A2 peptide complexes. *Int Immunol* 9: 451-459

Wang B, Maile R, Greenwood R, Collins E J and Frelinger J A (2000) Naive CD8+ve T cells do not require costimulation for proliferation and differentiation into cytotoxic effector cells. *J Immunol* 164: 1216-1222

Wang T L, Ling M, Shih I M, Pham T, Pai S I, Lu Z, Kurman R J, Pardoll D M and Wu T C (2000) Intramuscular administration of E7-transfected dendritic cells generates the most potent E7-specific anti-tumor immunity. *Gene Therapy* 7: 726-733

Wataya H, Kamikawaji N, Nakanishi Y, Takayama K, Hara N and Sasazuki T (2001). Quatitation of HLA-A*0201 bound tumor associated antigens on a peptide pulsed B cell line. *Hum Immunol* 62: 125-132

Wherry E J, Puorro K A, Porgador A and Eisenlohr L C (1999) The induction of virus specific CTL as a function of increasing epitope expression: responses rise steadily until excessively high levels of epitope are attained. *J Immunol* 163: 3735-3745

What is claimed is:

1. A method for attaching a complex to a target cell in vitro,
    wherein the complex comprises an HLA class I molecule or fragment thereof having a peptide binding groove, a recognition peptide, and attachment means comprising a linking polypeptide with high specific affinity for a target cell specific molecule on the surface of the target cell for selectively attaching said HLA class I molecule or fragment thereof to the target cell, wherein the said HLA class I molecule or fragment thereof is bound or attached to a recognition peptide in the peptide binding groove of said HLA class I molecule or fragment thereof, wherein the recognition peptide is arranged to be presented by said HLA class I molecule or fragment thereof for T cell recognition, and the HLA class I molecule or fragment thereof comprises a T cell binding portion, said method for attaching comprising the steps of:

(i) introducing onto the surface of said target cell said attachment means; followed by, (ii) introducing onto the surface of said target cell said HLA class I molecule or fragment thereof having bound or attached thereto the recognition peptide.

2. The method of claim 1 wherein the target cell is a B cell.

3. The method of claim 1 wherein the target cell is a tumor cell.

4. The method of claim 1 wherein the attachment means is an antibody or antigen binding fragment thereof that is linked or fused to a first small molecule, and wherein the HLA class I molecule or fragment thereof is joined to a second small molecule, wherein the first and second small molecules are each selected from biotin and avidin/streptavidin or calmodulin and calmodulin binding peptides.

5. A method for ex vivo amplification of cytotoxic T cells having affinity for an HLA complex or fragment thereof having a peptide binding groove that includes a recognition peptide in the binding groove of said HLA complex or fragment thereof, said method comprising isolating a mixed population of peripheral blood mononuclear cells comprising cytotoxic T cells and antigen presenting cells from a subject, attaching to the antigen presenting cells the HLA complex, wherein the HLA complex comprises an HLA class I molecule or fragment thereof having a peptide binding groove the recognition peptide, and attachment means comprising a linking polypeptide with high specific affinity for an antigen presenting cell specific molecule on the surface of the antigen presenting cell for selectively attaching said HLA class I molecule or fragment thereof to the antigen presenting cell, wherein the said HLA class I molecule or fragment thereof is bound or attached to a recognition peptide in the peptide binding groove of said HLA class I molecule or fragment thereof, wherein the recognition peptide is arranged to be presented by said HLA class I molecule or fragment thereof for T cell recognition, and the HLA class I molecule or fragment thereof comprises a T cell binding portion, and, said method comprising the steps of:

(i) introducing onto the surface of said antigen presenting cell said attachment means; followed by, (ii) introducing onto the surface of said antigen presenting cell said HLA class I molecule or fragment thereof having bound or attached thereto the recognition peptide, whereby cytotoxic T cells in the population of peripheral blood mononuclear cells are amplified.

6. The method of claim 5 wherein the antigen presenting cell is a B cell.

7. The method of claim 5 wherein the attachment means is an antibody or antigen binding fragment thereof that is linked or fused to a first small molecule, and wherein the HLA class I molecule or fragment thereof is joined to a second small molecule, wherein the first and second small molecules are each selected from biotin and avidin/streptavidin or calmodulin and calmodulin binding peptides.

* * * * *